US009494575B2

(12) United States Patent
Jin et al.

(10) Patent No.: US 9,494,575 B2
(45) Date of Patent: Nov. 15, 2016

(54) CELLS SCREENING METHOD

(75) Inventors: Aishun Jin, Toyama (JP); Hiroyuki Kishi, Toyama (JP);
(Continued)

(73) Assignees: TOYAMA PREFECTURE, Toyama (JP); VALNEVA, Lyon (FR)

( * ) Notice: Subject to any disclaimer, the term of this patent is extended or adjusted under 35 U.S.C. 154(b) by 1350 days.

(21) Appl. No.: 12/671,690

(22) PCT Filed: Aug. 1, 2008

(86) PCT No.: PCT/JP2008/063874
§ 371 (c)(1),
(2), (4) Date: Aug. 12, 2011

(87) PCT Pub. No.: WO2009/017226
PCT Pub. Date: May 2, 2009

(65) Prior Publication Data
US 2011/0294678 A1 Dec. 1, 2011

(30) Foreign Application Priority Data

Aug. 2, 2007 (JP) .................................. 2007-201493

(51) Int. Cl.
*C40B 30/04* (2006.01)
*C12N 5/0781* (2010.01)
(Continued)

(52) U.S. Cl.
CPC .................................. *G01N 33/5047* (2013.01)

(58) Field of Classification Search
CPC ................................................. G01N 33/5047
(Continued)

(56) References Cited

U.S. PATENT DOCUMENTS 4,529,712 A * 7/1985 Jou ...................... G01N 33/554
436/519
4,729,949 A 3/1988 Weinreb et al.
(Continued)

FOREIGN PATENT DOCUMENTS

EP 0258565 3/1988
EP 1566635 8/2005
(Continued)

OTHER PUBLICATIONS

Love et al., "A microengraving method for rapid selection of single cells producing antigen-specific antibodies", Nature Biotechnology, vol. 24, No. 6, p. 703-707 (2006).*
Rosenthal et al., "Cell patterning chip for controlling the stem cell microenvironment" Biomaterials, Elsevier Schence Pulishers BV. vol. 28, No. 21 Apr. 29, 2007, pp. 3208-3216, XP022051968.
Ostuni E et al., "Selective Deposition of Proteins and Cells in Arrays of Microwells" Langmuir, American Chemical Society, Wasington, DC, US, vol. 17, May 5, 2001, pp. 2828-2834, XP002535449.
Decaestecker et al., "Can anti-migratory drugs be screened in vitro? A review of 2D and 3D assays for the quantitative analysis of cell migration" Medical Research Reviews, vl. 27, No. 2 Mar. 2007, pp. 149-176, XP002599440.
Extended European Search Report for EP Application No. 08792087.2-2401/2184345, Sep. 23, 2010.
International Preliminary Report on Patentability (Chapter I) with Translation of Written Opinion of the International Searching Authority (w/ International Preliminary Report) for corresponding International Application No. PCT/JP2008/063874, Feb. 24, 2010.
Ostuni et al., "Selective Deposition of Proteins and Cells in Arrays of Microwells", Langmuir, 2001, vol. 17, pp. 2828-2834.
(Continued)

*Primary Examiner* — Larry Riggs
*Assistant Examiner* — Karla Dines
(74) *Attorney, Agent, or Firm* — Ditthavong & Steiner, P.C.

(57) ABSTRACT

Provided are a method and means permitting the simultaneous measurement of the reactive properties of more than 10,000 of antigen-stimulated lymphocytes being held on a chip. A microwell array comprises multiple wells capturing single cells and a coating layer on a principal surface around the wells containing a substance capable of binding to a substance produced by the cells in the wells. A method for screening a target cell comprises: causing specimen cells and a cell culture broth to be contained in the wells of the microwell array; culturing the cells in a state permitting the diffusion of substances from the wells into the coating layer; feeding a label substance binding specifically to a substance produced by a target cell onto the coating layer; and detecting the substance produced by the target cell by the label substance binding around the well to specify the target cell.

21 Claims, 19 Drawing Sheets

(75) Inventors: Atsushi Muraguchi, Toyama (JP);
Tsutomu Obata, Takaoka (JP)

(51) Int. Cl.
*C40B 60/12* (2006.01)
*G01N 33/50* (2006.01)
*C12N 5/10* (2006.01)
*C12N 5/071* (2010.01)
*C12N 5/16* (2006.01)

(58) Field of Classification Search
USPC .......................................................... 506/9
See application file for complete search history.

(56) References Cited

U.S. PATENT DOCUMENTS

| | | |
|---|---|---|
| 5,272,081 A | 12/1993 | Weinreb et al. |
| 5,310,674 A | 5/1994 | Weinreb et al. |
| 5,506,141 A | 4/1996 | Weinreb et al. |
| 6,087,103 A | 7/2000 | Burmer |
| 6,197,575 B1 | 3/2001 | Griffith et al. |
| 6,210,910 B1 | 4/2001 | Walt et al. |
| 6,232,066 B1 | 5/2001 | Felder et al. |
| 6,377,721 B1 | 4/2002 | Walt et al. |
| 6,410,252 B1 | 6/2002 | Lehmann et al. |
| 6,548,263 B1 | 4/2003 | Kapur et al. |
| 6,565,813 B1 | 5/2003 | Garyantes |
| 6,667,159 B1 | 12/2003 | Walt et al. |
| 2002/0072116 A1 | 6/2002 | Bhatia et al. |
| 2003/0017349 A1 | 1/2003 | Brown et al. |
| 2003/0027214 A1 | 2/2003 | Kamb |
| 2003/0030184 A1 | 2/2003 | Kim et al. |
| 2003/0032002 A1 | 2/2003 | Wang et al. |
| 2003/0064386 A1 | 4/2003 | Karaki et al. |
| 2003/0113833 A1 | 6/2003 | Oka et al. |
| 2003/0197170 A1 | 10/2003 | Bader et al. |
| 2005/0014201 A1* | 1/2005 | Deuthsch ............... G02B 21/34 435/7.2 |
| 2005/0112033 A1 | 5/2005 | Zhang et al. |
| 2005/0220675 A1 | 10/2005 | Reed et al. |
| 2005/0221271 A1 | 10/2005 | Murphy et al. |
| 2006/0078946 A1 | 4/2006 | Muraguchi et al. |
| 2006/0134704 A1 | 6/2006 | Muraguchi et al. |
| 2008/0014631 A1 | 1/2008 | Muraguchi et al. |
| 2009/0181859 A1 | 7/2009 | Muraguchi et al. |

FOREIGN PATENT DOCUMENTS

| | | |
|---|---|---|
| EP | 1691196 | 8/2006 |
| JP | 59-31685 | 2/1984 |
| JP | 63-106565 | 5/1988 |
| JP | 05-240869 | 9/1993 |
| JP | 06-21509 | 1/1994 |
| JP | 2003-033177 | 2/2003 |
| JP | 2005-253412 | 9/2005 |
| WO | WO 98/10284 | 3/1998 |
| WO | WO 99/45357 | 9/1999 |
| WO | WO 02/055653 | 7/2002 |
| WO | WO 02/078844 | 10/2002 |
| WO | WO 03/035824 | 5/2003 |
| WO | WO 2004/008791 | 1/2004 |
| WO | WO 2004/041061 | 5/2004 |
| WO | WO 2005/031349 | 4/2005 |
| WO | WO 2007/076411 | 7/2007 |

OTHER PUBLICATIONS

Chen et al., "A novel micro-well array chip for liquid phase biomaterial processing and detection", Sensors and Actuators, 2003, pp. 193-200, Elsevier.

Abbas et al., "Second Edition Cellular and Molecular Immunology", W.B. Saunders company, A division of Harcourt Brace & Company.

Clark et al., "Regulation of Human B-Cell Activation and Adhesion", Annu. Rev. Immunol, 1991, pp. 97-127, Downloaded from www.annualreviews.org.

Sredni et al., "Antigen-Specific, Proliferating T Lymphocyte Clones. Methodology, Specificity, MHC Restriction and Alloreactivity", Immunological Reviews, 1981, vol. 54, pp. 187-223.

Babcook et al., "A novel strategy for generating monoclonal antibodies from single, isolated lymphocytes producing antibodies of defined specificities", Proc. Natl. Acad. Sci., 1996, vol. 93, pp. 7843-7848, USA.

Jin et al., "Rapid isolation of antigen-specific antibody-secreting cells using a chip-based immunospot array", Nature Protocols, 2011, vol. 6, No. 5, pp. 668-676.

Tokimitsu et al., "Single Lymphocyte Analysis with a Microwell Array Chip", Cytometry Part A, 2007, pp. 1003-1010, 71A.

Steenbakkers et al., "A new approach to the generation of human or murine antibody producing hybridomas", Journal of Immunological Methods, 1992, pp. 69-77, 152.

Yano et al., "Lymphocyte Function Detection Methods", 1994, pp. 262-267, Chugai Igaku Corp., (w/ Statement of Relevancy).

Ishida et al., "Methods of Conducting Immunological Experiments I, II", published by Nankodo, 1995, pp. 742-747, (w/ Statement of Relevancy).

Altman et al., "Phenotypic Analysis of Antigen-Specific T Lymphocytes", Science, vol. 274, Oct. 4, 1996, pp. 94-96.

Abts et al., "CD20 positive human B lymphocytes separated with the magnetic cell sorter (MACS) can be induced to proliferation and antibody secretion in vitro", Journal of Immunological Methods, vol. 125, 1989, pp. 19-28.

Roome et al., "The use of Epstein-Barr virus transformation for the production of human monoclonal antibodies", Experimental Biology, vol. 43, 1984, pp. 35-55.

Carson et al., "Human Lymphocyte Hybridomas and Monoclonal Antibodies", Advances in Immunology, vol. 38, 1986, pp. 275-311.

Huston et al., "Protein engineering of antibody binding sites: Recovery of specific activity in an anti-digoxin single-chain Fv analogue produced in *Eschericha coli*", Proc. Natl. Acad. Sci. USA, vol. 85, Aug. 1988, pp. 5879-5883.

Yamamura et al., "Single-Cell Microarray for Analyzing Cellular Response", Anal. Chem, vol. 77, 2005, pp. 8050-8056.

* cited by examiner

A

Receptor
Microwell

B

Secreted antibody

C

Fluorescence labeled ligand

D

Fluorescence labeled ligand

Fig. 4-2
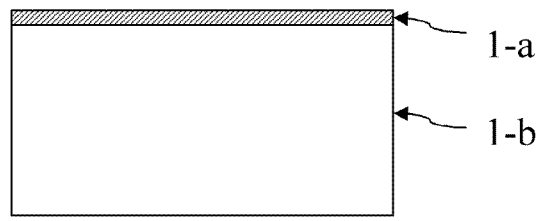
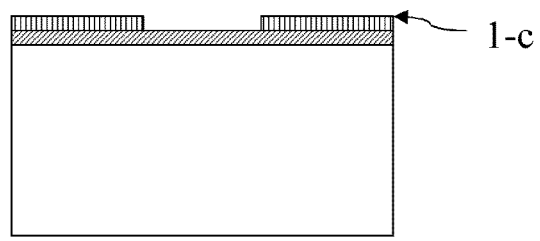
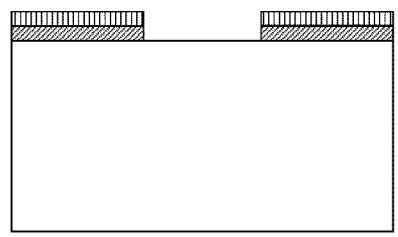
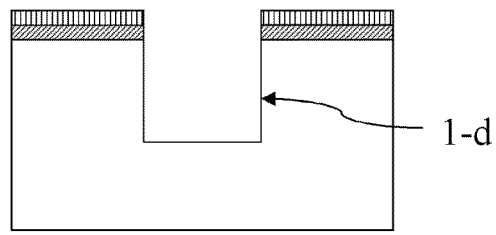
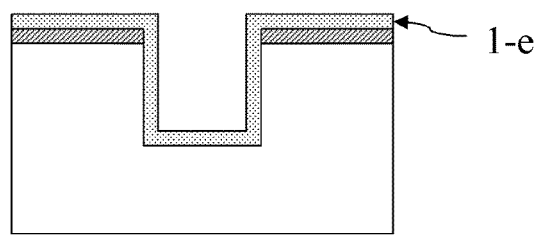

Fig. 5-1
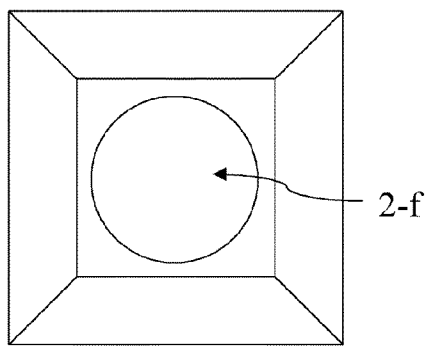
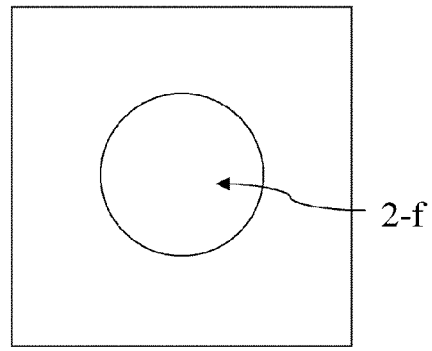
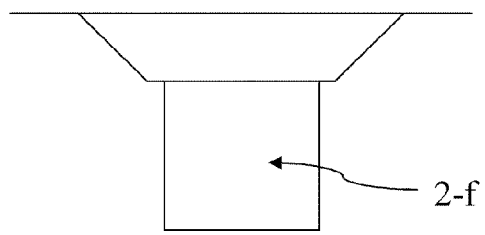
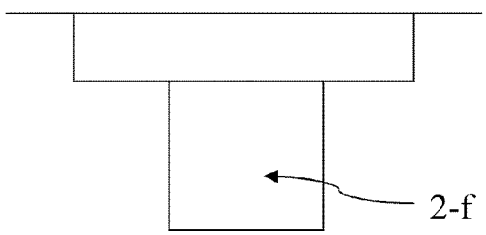

1,700 × 5.88 μm     10kV

Fig. 6-2
3-a
3-b
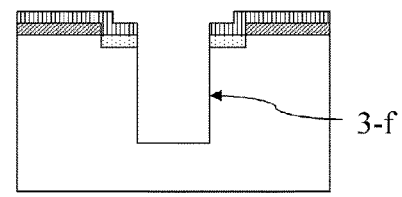
3-f
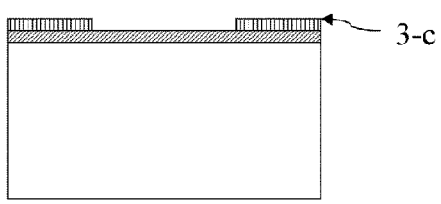
3-c
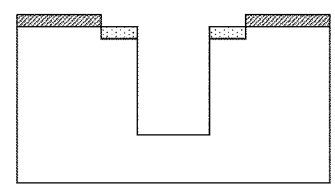
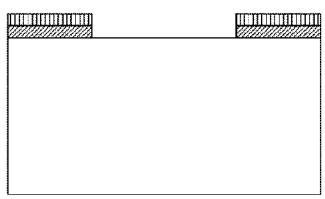
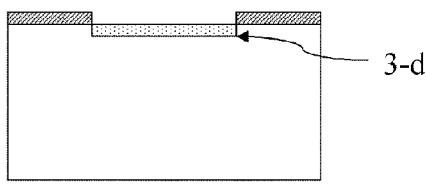
3-d
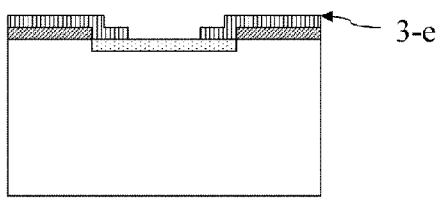
3-e 50 μm

110TC

HyHEL10
110TC

X63/116

A Detection of HEL specific antibody

B Detection of cells

C Combination of A and B

HEL-Ag ⟶ mHEL IgG ⟶ Anti mouse-IgG-cy3 ⟶ Detection

Mouse CD138+HEL derived cells-immunized mouse spleen

CELLS SCREENING METHOD

CROSS-REFERENCE TO A RELATED PATENT APPLICATION

The present application claims priority under Japanese Patent Application No. 2007-201493 filed on Aug. 2, 2007, the entire contents of which are hereby incorporated by reference.

TECHNICAL FIELD

The present invention relates to a method for screening cells, and to a microwell array employed in this method. More particularly, the present invention relates to a method for screening immune cells such as specific immunoglobulin-producing cells and specific cytokine-producing cells, and to a microwell array employed in this method.

BACKGROUND ART

Conventionally, antigen-specific antibody-producing hybridomas have been prepared to produce monoclonal antibodies. In the conventional method of preparing hybridomas, hybridomas are prepared, after which hybridoma clones producing antigen-specific antibodies are screened. However, the preparation of hybridomas is not efficient. That is, not all B lymphocytes become hybridomas; only some of the B lymphocytes in which cell fusion with a myeloma has occurred become hybridomas. Even when a hybridoma is produced with a spleen cell that has been stimulated with an antigen, not just antigen-specific antibody-producing hybridomas are produced; most of the hybridomas that are produced either produce unrelated antibodies or do not produce antibodies at all.

For example, when looking for a hybridoma producing a target antibody by the conventional method, spleen cells taken from an immunized mouse are subjected to cellular fusion with myelomas and sown into about ten 96-well plates. More could be sown if all the cells were used, but there are time limits when a single person is doing the screening, and those that remain are stored by freezing or the like. Normally, hybridomas grow in about 500 wells when using this method.

The hybridomas in the 500 wells do not all proliferate at the same speed; some grow quickly and others grow slowly. Accordingly, it is impossible to check the growth of all 500 simultaneously. First, a check must be made under a microscope as to which wells have produced cell growth, and whether the number of cells has increased sufficiently to check for antibodies. Subsequently, cell supernatant is collected from suitable wells, and a check is made for the production of antigen-specific antibodies. It is necessary to perform the cell check and cell supernatant check extremely rapidly. This is because hybridomas grow steadily and proliferate excessively if left alone, depleting the nutrients in the medium and dying out. Accordingly, screening must be completed before the desired hybridomas die.

Further, once a well is found in which a target hybridoma is growing, frequently there will be hybridomas producing other antibodies growing in the well in addition to the hybridoma producing the target antibody. Further, since hybridomas drop their own chromosomes while growing, there are also cases where a hybridoma that has been producing an antibody ends up losing the chromosome with the antibody and becomes unable to produce the antibody. The growth of such cells is often more rapid than that of hybridomas that are producing antibody, and most of the cells that are cultured when left alone end up becoming non-antibody-producing cells. Accordingly, when a well is discovered in which a desired hybridoma is growing, the cells in that well are immediately reseeded one cell per well in a 96-well plate (critical dilution method), and screening is conducted again for desired antibody-producing hybridomas (secondary screening). Once a targeted hybridoma has been detected, it is necessary to rapidly proceed through secondary screening before the state of the cell deteriorates.

As set forth above, since screening is sometimes conducted with just some of the hybridomas that are prepared, without screening them all, it becomes difficult to obtain low-frequency antigen-specific antibody-producing hybridomas.

More specifically, in the case of human antigen-specific antibodies, there exists a method of screening cells producing antigen-specific antibodies in strains developed by transforming peripheral B lymphocytes with EB virus (Non-patent Document 1). In this method, since the frequency of the lymphocyte cell strains established is low, the probability of obtaining an antigen-specific antibody-producing B lymphocyte cell strain is extremely low. Further, it takes about a month to establish a cell strain. Still further, the B lymphocyte strains that are established produce only small quantities of antibody. Although hybridomas can be prepared for mice, no system for producing hybridomas with good efficiency has been developed for humans.

Hybridomas can be prepared for mice. Conventionally, to produce a hybridoma, a mouse is immunized with an antigen, the spleen or lymph nodes of the mouse are removed, lymphocytes are prepared, about $10^8$ of the lymphocytes prepared and about $10^7$ myeloma cells are fused using polyethylene glycol or by subjecting them to a voltage, they are cultured in a selection medium such as HAT, the hybridomas that grow are screened by ELISA, flow cytometry, or the like to determine whether or not they are producing the antigen-specific antibody, and the antigen-specific antibody-producing hybridomas are selected (Non-patent Documents 2 and 3). When employing this method, hybridomas grow in 300 to 400 wells. Of these, hybridomas producing antigen-specific antibodies grow in only several percent of the wells. This number varies with the antigen employed, but, it is difficult to prepare hybridomas by this method when the frequency of the antigen-specific antibody-producing B lymphocyte is low.

Accordingly, the present inventors examined methods of conveniently selecting lymphocytes reacting specifically with prescribed antigens in the form of both antigen-specific lymphocytes of relatively high frequency and antigen-specific lymphocytes of low frequency, and preparing antigen-specific antibody-producing hybridomas from the antigen-specific B lymphocytes that were selected. They then devised a method for preparing antigen-specific antibody-producing hybridomas by culturing selected antigen-specific B lymphocytes and fusing the antigen-specific B lymphocytes grown by culturing with myeloma cells to prepare hybridomas, and applied for a patent (Patent Document 1).

Attempts have also been made to specify and select individual cells, and use the cells that have been selected. For example, the separate detection of individual antigen specificity, the recovery of a single detected antigen-specific lymphocyte, and the use of the single antigen-specific lymphocyte recovered to prepare an antibody, for example, have been examined (Patent Documents 2 and 3).

[Patent Document 1] WO2004/087911
[Patent Document 2] Japanese Patent Un-examined Publication 2004-173681
[Patent Document 3] Japanese Patent Un-examined Publication 2004-187676
[Non-patent Document 1] "Methods of Detecting Lymphocyte Functions (Version 5)", Junichi YANO, Michio FUJIWARA, eds., Chugai Igakusha (1994), "Use of EB virus transform B cells for preparation of human monoclonal antibody", Fumio MIZUNO, Toshiro OHSATO, pp 381-391.
[Non-patent Document 2] "Methods of Detecting Lymphocyte Functions (Version 5)", Junichi YANO, Michio FUJIWARA, eds., Chugai Igakusha (1994), "Preparation of monoclonal antibody with B cell hybridomas", Hideo NARIUCHI, pp 574-576
[Non-patent Document 3] Monoclonal antibodies in "Antibodies: A Laboratory Manual" by Ed Harlow and David Lane, Cold Spring Harbor Laboratory, Cold Spring Harbor, N.Y., pp 139-pp 244, 1988
[Non-patent Document 4] In vitro antibody production. In Current Protocols in Immunology. Edited by J. E. Coligan et al., John Wiley & Sons (New York), p. 3.8.1-3.8.16, 1991.
[Non-patent Document 5] Babcook, J. S., Leslie, K. B., Olsen, O. A., Salmon, R. A., Schrader, J. W. A novel strategy for generating monoclonal antibodies from single, isolated lymphocytes producing antibodies of defined specificities. Proc Natl Acad Sci USA, 93: 7843-7848, 1996.
[Non-patent Document 6] Measurement of polyclonal immunoglobulin synthesis using the ELISPOT assay. In Current Protocols in Immunology. Edited by J. E. Coligan et al., John Wiley & Sons (New York), p. 7.14.1-7.14.7, 1991.
[Non-patent Document 7] Assays for antibody production. In Current Protocols in Immunology. Edited by J. E. Coligan et al., John Wiley & Sons (New York), p. 2.1.1-2.1.22, 1991.
[Non-patent Document 8] J. C. Love, J. L. Ronan, G. M. Grotenbreg, A. G. van der Veen, H. L. Ploegh, A microengraving method for rapid selection of single cells producing antigen-specific antibodies. Nature Biotechnology, 24: 703-707, 2006.

The entire contents of Patent Documents 1-3 and Non-patent Documents 1-8 are hereby incorporated by reference.

In the above-described conventional methods, the separate detection of the antigen specificity of individual lymphocytes and the recovery of the antigen-specific lymphocytes that are detected are conducted manually. In Patent Documents 2 and 3, it is stated that the specification of cells at the cellular level has been confirmed, and that it is also possible to recover the specified cells. However, the actual detection of those lymphocytes that have specifically reacted with an antigen from among numerous lymphocytes is difficult.

As an example of a detection method, the fact that the calcium ion concentration rises in lymphocytes that have reacted with an antigen is exploited, this change in calcium ion concentration is detected by fluorescence, and antigen-specific lymphocytes are specified. However, depending on the type of cell (lymphocyte), the method of generating fluorescence, the intensity thereof, and the like may differ. There are lymphocytes in which the calcium ion concentration rises immediately upon antigen stimulation, resulting in an increase in the intensity of fluorescence. However, there are also cells in which the calcium ion concentration rises only after a certain period has elapsed following antigen stimulation, resulting in a rise in the intensity of fluorescence. Further, it is necessary to measure nearly simultaneously and in one shot the intensity of fluorescence of about 10,000 to 200,000 lymphocytes being held on the surface of a several centimeter square tube. Still further, since this fluorescence arises in individual cells, the intensity of the fluorescence is low, requiring highly sensitive fluorescence detection.

Thus far, there exists neither a method nor a device capable of simultaneously measuring the intensity of numerous sources of weak fluorescence gathered in highly concentrated fashion on the surface of a tube.

One conventional device is the laser scanning cytometer. With a laser scanning cytometer, it is possible to measure the concentration of calcium in several hundred thousand individual cells. However, a single scan requires a lengthy 10 minutes or more, precluding real-time detection in lymphocytes the fluorescence intensity of which changes several minutes after antigen stimulation.

A fluorescent microscope with projector is comprised of an ordinary fluorescent microscope combined with a projection device. A fluorescent microscope with projector presents no problem in terms of speed. However, as an ordinary microscope, the scope of projection is narrow, making it possible to detect fluorescence in only about 1,000 cells at a time. It is impossible to detect fluorescence in several tens of thousands to several hundred thousand cells at a time.

A cell chip detector based on a DNA microarray scanner is a device that has been developed to detect fluorescence in cells arrayed in cell chips, and can detect fluorescence inside or outside cells. However, it is a system that excites a fluorescent dye with a laser and detects the excitation light. Thus, in detection systems that track changes over time, the line scanning rate of the laser is slow, precluding the simultaneous detection of numerous cell regions.

In the methods described in above-cited Patent Documents 2 and 3, the reaction detection system for detecting cells reacting specifically to an antigen is required to have the ability to capture in real time changes in calcium over time within individual cells and the ability to detect individual cells that are present in only small number (react only slightly) among large numbers of cells, necessitating the ability to separately and simultaneously analyze large numbers of cells in parallel.

Accordingly the object of the present invention is to provide a method permitting the simultaneous measurement of the states of a large number of cells, exceeding 10,000 and desirably exceeding 100,000, being held on a chip, such as the reactive properties of antigen-stimulated lymphocytes, and the separate determination of the states of individual cells.

B lymphocytes express a single antibody on the cell surface. When a pathogen (antigen) or the like invades the body, the antigen binds to the antibody on the cell surface, activating the cell and causing it to proliferate and differentiate. Finally, it differentiates into an antibody-secreting cell. There exist already numerous methods of specifying antibody-secreting cells. Typical methods of specifying single antibody-secreting cells are the plaque method and the Enzyme-Linked Immunospot (ELISPOT) method.

The plaque method is a method of specifying antigen-specific antibody-secreting cells in which hemolysis induced by binding antibodies to erythrocytes that have been labeled with the antigens surrounding antibody-secreting cells is employed as an indicator (Non-patent Document 4). A method that detects antigen-specific antibody-secreting cells by the plaque method and recovers the antibody gene has already been developed (Non-patent Document 5).

The ELISPOT method is a method of inoculating cells on a plate that has been coated with antigen, causing the antibody that is secreted by antibody-secreting cells to bind to the antigen around the cells, and detecting this with enzyme-labeled anti-Ig antibody or the like (Non-patent Document 6). With the ELISPOT method, in the course of detecting the binding of antigen-specific antibody around cells with enzyme-labeled anti-Ig antibody, the cells themselves get washed away, precluding recovery of the antigen-specific antibody-secreting cells.

Hybridomas are antibody-secreting cells. However, in the course of screening hybridomas, enzyme-linked immunosorbent assay (ELISA) is commonly employed (Non-patent Document 7). Recently, this method has been further developed; a method has been reported whereby individual hybridomas are cultured in small wells, and the antibody that is secreted in each well is detected by an antigen or the like labeled with a fluorescent label to detect antigen-specific antibody-secreting cells (Non-patent Document 8).

To achieve the above-stated object of the present invention, the present inventors conducted extensive research into providing a method for detecting immune cells, such as new antigen-specific antibody-secreting cells, that was completely different from the methods described in Non-patent Documents 4 to 8. The present invention was devised on that basis.

DISCLOSURE OF THE INVENTION

The present invention, devised to solve the above-stated problems, is set forth below:

[1] A microwell array, comprising multiple wells on one of the principal surfaces of a base member, the wells being of a size permitting the entry of only a single cell into each well, characterized in that:
a coating layer of a substance capable of binding to at least part of a substance produced by at least a portion of the cells contained in the wells is present on at least part of the principal surface at least around the wells.

[2] The microwell array according to [1] which is used:
to contain cells and cell culture solution in at least a portion of the wells thereof;
to immerse the coating layer and the wells in the culture solution and culture the cells in a state permitting the diffusion of a substance contained in the culture solution into the coating layer; and
once the culture solution has been removed following culturing, to detect the presence or absence of binding between a substance that has been produced by at least a portion of the cells contained in the wells and the substance in the coating layer.

[3] The microwell array according to [1] or [2], wherein at least a portion of the cells contained in the wells are immunoglobulin-producing cells or cytokine-producing cells.

[4] The microwell array according to [1] or [2], wherein at least a portion of the cells contained in the wells are immunoglobulin-producing cells, and the substance having the ability to bind to at least a portion of a substance produced by the immunoglobulin-producing cells is an anti-immunoglobulin antibody or antigen.

[5] The microwell array according to [4], wherein the detection of the presence or absence of the binding is conducted using an antigen or an antibody to the immunoglobulin that is produced.

[6] The microwell array according to [1] or [2], wherein at least a portion of the cells contained in the wells are cytokine-producing cells, and the substance having the ability to bind to at least a portion of the substance produced by the cytokine-producing cells is an anti-cytokine antibody or a cytokine receptor.

[7] The microwell array according to [6], wherein the detection of the presence or absence of the binding is conducted using a cytokine receptor or an antibody to the cytokine produced.

[8] The microwell array according to [1] or [2], wherein at least a portion of the cells contained in the wells are immunoglobulin-producing cells, and the substance having the ability to bind to at least a portion of the substance produced by the immunoglobulin-producing cells is a cytokine receptor or a receptor.

[9] The microwell array according to [8], wherein the detection of the presence or absence of the binding is conducted using a cytokine or a ligand.

[10] The microwell array according to any one of [1] to [9], wherein the immunoglobulin-producing cells and the cytokine-producing cells are natural cells or hybridomas.

[11] The microwell array according to any one of [1] to [10], wherein the base member is plate-shaped.

[12] The microwell array according to any one of [1] to [11], wherein at least a portion of the principal surface on which is not present a coating layer of the substance having the ability to bind to at least a portion of the substance produced by the cells stored in the wells is coated with a blocking agent.

[13] A method of screening for a target cell, comprising:
causing specimen cells and a cell culture broth to be contained in at least a portion of the wells of a microwell array comprising multiple wells, each well being of a size permitting the entry of only a single cell therein, on one of the principal surfaces of a base member, and comprising a coating layer of a substance having the ability to bind to at least a portion of a substance produced by a target cell on at least a portion of the principal surface at least around the wells;
immersing the coating layer and the wells in the culture broth and culturing the cells in a state permitting the diffusion of substances in the culture broth from the wells into the coating layer;
after optionally removing the culture broth, feeding a label substance binding specifically to a substance produced by a target cell present among the specimen cells onto the coating layer; and
detecting the substance produced by the target cell that has bound to the substance in the coating layer by means of the label substance to specify the target cell.

[14] The screening method according to [13], wherein the cells present among the specimen cells include cells that have been stimulated with a desired antigen in advance and are in a state capable of producing a substance.

[15] The screening method according to [13] or [14], wherein the specimen cells include immunoglobulin-producing cells or cytokine-producing cells.

[16] The screening method according to [13] or [14], wherein the specimen cells include immunoglobulin-producing cells, a substance having the ability to bind to at least a portion of the substance produced by the target cell is an anti-immunoglobulin antibody or antigen, and the target cell is an antigen-specific immunoglobulin-producing cell.

[17] The screening method according to [16], wherein the detection of the presence or absence of the binding is conducted using antigen or an antibody to the immunoglobulin that is produced.

[18] The screening method according to [13] or [14], wherein the specimen cells include immunoglobulin-producing cells, the substance having the ability to bind to at least a portion of the substance produced by the target cell is a cytokine receptor or receptor, and the target cell is an antigen-specific immunoglobulin-producing cell.

[19] The screening method according to [18], wherein the detection of the presence or absence of the binding is conducted using a cytokine or a ligand.

[20] The screening method according to [13] or [14], wherein the specimen cells include cytokine-producing cells, the substance having the ability to bind to at least a portion of the substance produced by the target cell is an anti-cytokine antibody or a cytokine receptor, and the target cell is an antigen-specific cytokine-producing cell.

[21] The screening method according to [20], wherein the detection of the presence or absence of the binding is conducted using an antibody to the cytokine produced or a cytokine receptor.

[22] The screening method according to any one of [13] to [21], wherein the immunoglobulin-producing cells and cytokine-producing cells are natural cells, hybridomas, or cell strains.

[23] A method for producing a target cell, comprising recovering from a well a target cell specified by the screening method in accordance with any one of [13] to [22].

[24] The production method in accordance with [23], wherein the target cell is a specific immunoglobulin-producing cell or specific cytokine-producing cell.

The present invention provides a method and a means permitting the simultaneous measurement of the states of a large number of cells, exceeding 10,000, for example, and desirably exceeding 100,000, being held on a chip, such as the reactive properties of antigen-stimulated lymphocytes, and the separate determination of the states of individual cells.

BEST MODES OF CARRYING OUT THE INVENTION

[The Microwell Array]

The microwell array of the present invention is a microwell array having multiple wells on one of the principal surfaces of a base member, the wells being of a size permitting the entry of only a single cell. A microwell array having such a structure may be employed in the form described in Patent Documents 1 to 3, for example.

Multiple microwells are disposed in equally spaced rows and columns on a microwell array chip.

Neither the shape nor the size of the microwells is specifically limited. However, for example, the shape of the microwell can be cylindrical. It can also be noncylindrical, such as a polyhedron comprised of multiple faces (for example, a parallelepiped, hexagonal column, or octagonal column), an inverted cone, an inverted pyramid (inverted triangular pyramid, inverted square pyramid, inverted pentagonal pyramid, inverted hexagonal pyramid, or an inverted polygonal pyramid with seven or more angles), or have a shape combining two or more of these shapes. For example, it may be partly cylindrical, with the remainder having the shape of an inverted cone. In the case of an inverted conical or an inverted pyramidal shape, the mouth of the microwell is on the bottom. However, the shape may be one in which a portion of the top of an inverted cone or inverted pyramid is cut off (in which case the bottom of the microwell is flat). For conical and parallelepiped shapes, the bottom of the microwell is normally flat, but curved surfaces (convex or concave) are also possible. The reason the bottom of the microwell is made curved is the same as for shapes consisting of an inverted cone or inverted pyramid with a portion of the top cut off.

For a cylindrically-shaped microwell, the dimensions can be, for example, a diameter of 3 to 100 micrometers. When the organic cell is a B lymphocyte, the diameter is desirably 4 to 15 micrometers. Further, the depth can be from 3 to 100 micrometers, and in the case where the organic cell is a B lymphocyte, the depth is desirably 4 to 40 micrometers. However, the dimensions of the microwell, as set forth above, can be suitably determined in consideration of a desirable ratio of the diameter of the organic cell to be contained in the microwell to the dimensions of the microwell.

The shape and size of the microwell are suitably determined in consideration of the type of organic cell (shape, size, and the like of the organic cell) to be stored in the microwell so that a single organic cell will be contained per microwell.

To ensure that a single organic cell will be contained per microwell, for example, the diameter of the largest circle that can be inscribed in the planar shape of the microwell suitably falls within a range of 0.5 to 2-fold, desirably 0.8 to 1.9-fold, and preferably, 0.8 to 1.8-fold the diameter of the organic cell to be contained in the microwell.

Further, the depth of the microwell suitably falls within a range of 0.5 to 4-fold, desirably 0.8 to 1.9-fold, and preferably, 0.8 to 1.8-fold the diameter of the organic cell to be contained in the microwell.

The number of microwells present in a single microwell array chip is not specifically limited. However, when the organic cell is a lymphocyte and the frequency of a given antigen-specific lymphocyte per $10^5$ cells is from 1 to about 500 at the high end, the number of microwells can range from about 2,000 to 1,000,000 per $cm^2$, for example.

The microwell array of the present invention further comprises, on at least a portion of the principal surface thereof around the wells, a coating layer of a substance having the ability to bind to at least a portion of a substance produced by at least a portion of the cells contained in the wells. This is a characteristic of the microwell array of the present invention.

In the microwell array of the present invention, the base member can be a plate (but there is no intent to limit it to a plate), and a coating layer is provided on at least a portion of the principal surface around the multiple wells provided on a principal surface of the base member. The microwell array of the present invention is employed to detect the presence or absence of binding between a substance produced by at least a portion of the cells contained in the wells and a substance in the coating layer.

The cells contained in the wells (specimen cells) can be, for example, a cell group containing immunoglobulin-producing cells or cytokine-producing cells. Further, the immunoglobulin-producing cells and cytokine-producing cells can be natural cells, hybridomas, or cell strains. Natural cells can be mammalian cells, such as cells collected from humans, mice, or the like. Hybridomas can be created by the usual methods described in the background art. Cell strains can be strains into which an expression-type cDNA library or the like has been genetically introduced.

When the cells contained in the wells are specimen cells including immunoglobulin-producing cells, an antigen or an anti-immunoglobulin antibody capable of reacting to immunoglobulin in the form of a substance produced by immunoglobulin-producing cells can be employed as the substance having the ability to bind to at least a portion of the substance produced by the cells. The presence or absence of the binding is detected using an antigen or an antibody to the immunoglobulin produced.

When the cells contained in the wells are specimen cells including cytokine-producing cells, an anti-cytokine antibody capable of reacting to the cytokine that is the substance produced by the cytokine-producing cells, or receptors, can be employed as the substance having the ability to bind to at least a portion of the substance produced by the cells. The presence or absence of the binding is detected using an antibody to the cytokine or a cytokine receptor.

Or, when the cells contained in the wells are specimen cells including immunoglobulin-producing cells, the substance having the ability to bind to at least a portion of the substance produced by the cells can be a receptor or cytokine receptor that is capable of reacting with the immunoglobulin that is produced by the immunoglobulin-producing cells. In that case, the presence or absence of bonds is detected using a ligand or cytokine capable of reacting with the receptor or cytokine receptor. When the immunoglobulin produced binds to the receptor or cytokine receptor, binding to the ligand or cytokine used to detect the presence or absence of binding is blocked, permitting detection of the presence or absence of binding.

Examples of:
(1) substances having the ability to bind to at least a portion of the substance produced by the cells (binding substance);
(2) cells stored in the wells (specimen cells);
(3) substances produced by the cells (produced substances); and
(4) label substances (label substances) for identifying produced substances are given in Table 1 below.

The substance used to label substances for identifying the produced substance can be a fluorescent substance, for example. However, it is not limited to fluorescent substances, and other label substances are possible. The labeling with a fluorescent substance such as an antigen or antibody serving as the label substance can be conducted by the usual methods. There are cases where the label substance binds specifically to the produced substance, and cases where it binds specifically to the binding substance.

TABLE 1

| Binding substance | Cell | Produced substance | Label substance |
| --- | --- | --- | --- |
| Anti-immunoglobulin Antibody | B lymphocyte | Immunoglobulin (antibody) All antibodies such as IgG, IgM, IgA, IgE | Antigen |
| Anti-immunoglobulin Antibody | B lymphocyte | Immunoglobulin (antibody) All antibodies such as | Anti-immunoglobulin antibody |

TABLE 1-continued

| Binding substance | Cell | Produced substance | Label substance |
| --- | --- | --- | --- |
| | | IgG, IgM, IgA, IgE | |
| Anti-IgG antibody | B lymphocyte | IgG | Antigen |
| Anti-IgG antibody | B lymphocyte | IgG | Anti-IgG antibody |
| Anti-IgM antibody | B lymphocyte | IgM | Antigen |
| Anti-IgM antibody | B lymphocyte | IgM | Anti-IgM antibody |
| Anti-IgA antibody | B lymphocyte | IgA | Antigen |
| Anti-IgA antibody | B lymphocyte | IgA | Anti-IgA antibody |
| Anti-IgE antibody | B lymphocyte | IgE | Antigen |
| Anti-IgE antibody | B lymphocyte | IgE | Anti-IgE antibody |
| Anti-cytokine antibody | T lymphocyte, others | Cytokine | Anti-cytokine antibody |
| Anti-cytokine antibody | T lymphocyte, others | Cytokine | (Soluble) cytokine receptor |
| (Soluble) cytokine receptor | T lymphocyte, others | Cytokine | Anti-cytokine antibody |
| Antigen | B lymphocyte | IgG | Anti-IgG antibody |
| Antigen | B lymphocyte | IgM | Anti-IgM antibody |
| Antigen | B lymphocyte | IgA | Anti-IgA antibody |
| Antigen | B lymphocyte | IgE | Anti-IgE antibody |
| (Soluble) cytokine receptor | B lymphocyte | Antibody | Cytokine* |
| (Soluble) receptor | B lymphocyte | Antibody | Ligand** |

*Detection of antibody blocking binding of cytokine
**Detection of antibody blocking binding of ligand In forming the coating layer of a binding substance, the principal surface of the base plate on which the coating layer is to be formed is treated with a silane coupling agent, for example, to ensure binding of the binding substance and the principal surface. Next, a solution containing the binding substance can be applied to the surface that has been treated with the silane coupling agent to form the coating layer. The amount of the coating of binding substance in the coating layer can be suitably determined based on the type of binding substance, the type of cell and the produced substance, and the type of label substance. The surface treatment to ensure binding of the binding substance to the principal surface is not limited to treatment with a silane coupling agent; any substance promoting binding of a binding substance comprised of protein or the like to the surface of a base plate comprised of an inorganic material (such as a silicon material) or an organic material (such as a polymer material) can be suitably selected for use.

On the surface that is coated with the binding substance, there may be cases where the binding substance may not be densely covered, with portions of uncovered surface remaining depending on the amount of the coating. In such cases, particularly when the surface has been treated with a silane coupling agent as set forth above, there are cases where the substance produced by the cells will bind nonspecifically to the surface of the base plate. Such nonspecific binding causes a decrease in the precision of detection sensitivity. Accordingly, in the present invention, at least a portion of the principal surface not having a coating layer of a substance having the ability to bind to at least part of the substance produced by the cells that are contained in the wells is desirably coated with a blocking agent. An example of a blocking agent is the water-soluble polymer Lipidure (registered trademark) having a structural unit in the form of 2-methacryloyloxyethylphosphorylcholine (MPC) with the same structure as the polar base of the phosphatidylcholine constituting the cellular membrane.

[The Screening Method]

The screening method of the present invention employs the microwell array of the present invention to screen out a target cell from a group of cells containing specimen cells; it comprises the following steps:
(1) causing specimen cells and cell culture broth to be contained in at least a portion of the wells of the microwell array;
(2) immersing the coating layer and the wells in culture broth and culturing the cells for some period in a state permitting the diffusion of substances contained in the culture broth from the cells into the coating layer;
(3) after removing the culture broth, feeding a label substance binding specifically to the substance produced by target cells present among the specimen cells into the coating layer; and
(4) detecting a substance that has been produced or secreted by the target cells and bound to the substance in the coating layer with the label substance to specify the target cell.

The (1) substance having the ability to bind to at least a portion of a substance produced by a cell (binding substance); (2) cells contained in the wells (specimen cells); (3) substance produced by the cells (produced substance); and (4) substance identifying the produced substance that has been labeled (label identification substance) employed in the screening method of the present invention are identical to those described for the microwell array of the present invention, and the items given in Table 1 are examples thereof.

Step (1)

Cells (a cell group) including specimen cells are introduced with a cell culture broth into at least a portion of the wells of a microwell array. Prior to introducing the cells, the wells of the microwell array and the area around them are cleaned with medium; adequate removal of impurities that have adhered to the surface in the course of forming the coating layer of a binding substance is desirable for accurate detection. The cells are introduced with culture broth into the wells. The specimen cells that are contained in the wells can be comprised of a cell group containing immunoglobulin-producing cells or cytokine-producing cells. Further, the immunoglobulin-producing cells and cytokine-producing cells can be natural cells or hybridomas. These cell groups can be obtained by known methods.

The cells that are contained in the wells can be cells that have been stimulated with a desired antigen in advance to induce a state permitting substance production. For example, in the case of immunoglobulin-producing cells, they are desirably cells that have been stimulated with a desired antigen in advance to induce a state permitting the production of immunoglobulin. Similarly, in the case of cytokine-producing cells, they are desirably cells that have been stimulated with a desired antigen in advance to induce a state permitting the production of cytokine. The desired antigen is not specifically limited; various desired members of the group consisting of proteins, sugars, lipids, nucleic acids, organic compounds, inorganic compounds, and combinations thereof (including cells) can be suitably selected. The culture broth can be suitably determined based on the types of cells that are being introduced and detected.

Step (2)

The coating layer and wells are immersed in the culture broth and the cells are cultured in a state permitting the diffusion of substances contained in the culture broth from the wells into the coating layer. The cultured cells produce substances and the substances that are produced are released into the culture broth, diffusing from the wells into the coating layer around the wells. The produced substances that diffuse and reach the coating layer bind to the binding substances constituting the coating layer. The culture conditions can be suitably determined based on the type of cell.

The culture period can be suitably determined to yield a detectable quantity of produced substance bound to the binding substance constituting the coating layer. In the coating layer around wells containing cells that do not produce the substance, no binding takes place between a produced substance and the binding substance. An excessively long culture period results in excessively wide diffusion of the produced substance, sometimes making it difficult to specify those wells containing cells producing the produced substance. The culture period is desirably suitably determined within a range permitting the ready specification of those wells containing cells producing the produced substance.

Step (3)

Once culturing has ended, after optionally removing the culture broth, a label substance binding specifically to the substance produced by the target cells present among the specimen cells is fed into the coating layer. The substance produced by the target cells disperses during culturing, binding to the binding substance constituting the coating layer. By feeding a label substance at this stage, the label substance binds to the produced substance that has bound to the coating layer, or binds to the coating layer that has not been blocked by the produced substance bound to the coating layer. In the former case, the label substance will sometimes bind to the produced substance. In the latter case, the label substance binds not to the produced substance, but to the binding substance constituting the coating layer. This point is described in detail further below.

Before feeding the label substance, it is desirable to remove the culture broth. When cells contained in the wells are immunoglobulin-producing cells, for example, large amounts of antibody will be secreted into the culture broth. When anti-immunoglobulin antibody is added, for example, it ends up binding to the antibody in the culture broth before it binds to the antibody on the chip surface, and may preclude detection of antibody bound to the chip surface. However, there are cases where detection can be conducted without problem by combining cells and binding substances even when the label substance is fed into the coating layer without removing the culture broth.

Step (4)

The substance produced by the target cell that has bound to the substance in the coating layer is detected by means of the label substance and the target cell is specified. The label substance binds to the produced substance that has bound to the coating layer. Accordingly, it is possible to specify the cell (target cell) producing the produced substance binding to the coating layer by detecting the label substance.

When the label substance is a substance binding specifically to the produced substance, the label substance binds to the produced substance that has diffused from the wells into the coating layer around the wells, reached the coating layer, and bound to the binding substance constituting the coating layer. This bound label substance is detected. Additionally, there is no binding of produced substance and binding substance in the coating layer around wells in which no substance is produced. Thus, there is no binding of the label substance, and no label substance is detected.

When the label substance is a substance binding specifically to the binding substance, the produced substance that has diffused from the wells into the coating layer around the wells, reaching the coating layer and binding to the binding substance constituting the coating layer, blocks binding of the label substance and the binding substance. Additionally, there is no binding of produced substance and binding substance in the coating layer around wells in which no produced substance has been produced. Thus, the binding of label substance and binding substance is not blocked, and the label substance binds. In this case, no label substance is detected in wells in which the produced substance has been produced, distinguishing them from wells in which the label substance is detected.

When the label substance is a fluorescent label, for example, the target cells can be specified with a fluorescence microscope, fluorescent image scanner, image reader, or the like.

In the embodiments described further below, chips with regular hexagonally shaped wells (lower left in FIG. 1) are primarily employed. In this case, the signal spreads in nearly concentric circle fashion (upper left in FIG. 1). However, as indicated on the lower right in FIG. 1, when a diagonal slit is formed in a regular hexagonal well, the antibody or the like that is produced also spreads in the direction of the slit, yielding a shape such as the Milky Way system shown in the upper right of FIG. 1. In this manner, the signal from the label substance obtained via the product varies in shape based on the shape of the well.

When the Label Substance is a Substance Binding Specifically to the Produced Substance (1)

When the specimen cells contained in the wells include immunoglobulin-producing cells, culturing the cells results in the production of immunoglobulin. By using a coating layer with an anti-immunoglobulin antibody or antigen as the binding substance, the immunoglobulin that is produced binds to the coating layer, and the immunoglobulin that has been produced and has bound to the coating layer can be detected using an antibody to the immunoglobulin or an antigen. Around wells containing cells that do not produce immunoglobulin, that is, around wells containing cells that do not produce immunoglobulin when stimulated with the antigen that has been provided, there is no immunoglobulin that has diffused from the wells. These wells can be distinguished from wells containing cells that produce immunoglobulin. In this manner, it is possible to specify target cells in the form of antigen-specific immunoglobulin-producing cells.

A more specific description will be given using FIG. 2.

(A) Antibody-secreting cells are poured into the individual wells of a microwell array chip made of silicon to the surface of which anti-immunoglobulin (Ig) antibody has been bound.

(B) The cells are cultured, causing them to secrete antibody. The antibody that is secreted by the cells binds to the anti-1 g antibody around the wells.

(C) When fluorescence-labeled antigen is added, the antigen binds to the antigen-specific antibody that has been trapped around the wells.

(D) Observation by fluorescence microscopy, scanning, or the like reveals that the antigen-specific antibody has spread into a donut shape around the wells.

When the Label Substance is a Substance Binding Specifically to the Produced Substance (2)

When the specimen cells contained in the wells include cytokine-producing cells, culturing the cells results in the production of cytokine. By using a coating layer with an anti-cytokine antibody or cytokine receptor as the binding substance, the cytokine that is produced binds to the coating layer, and the cytokine that has been produced and bound to the coating layer can be detected using an antibody to the cytokine or a cytokine receptor. Around wells containing cells that do not produce cytokine, that is, wells containing cells that do not produce cytokine when stimulated with the antigen that has been provided, no cytokine diffuses from the wells. These wells can be distinguished from wells containing cells that produce cytokine. In this manner, it is possible to specify target cells in the form of cytokine-producing cells.

When the Label Substance is a Substance Binding Specifically to the Binding Substance When the specimen cells contained in the wells include immunoglobulin-producing cells, culturing the cells results in the production of immunoglobulin. By using a coating layer with a cytokine receptor or receptor as the binding substance, a portion of the immunoglobulin that is produced binds to the coating layer, and the portion of the immunoglobulin that has been produced and has bound to the coating layer blocks binding of the cytokine receptor or receptor to the label substance in the form of a cytokine or a ligand. The label substance does not bind around wells containing cells producing immunoglobulin. Around wells containing cells that do not produce immunoglobulin, that is, wells containing cells that do not produce immunoglobulin when excited with the antigen that has been provided, no immunoglobulin disperses from the wells, and the binding of cytokine receptor or receptor and cytokine or ligand is not blocked. Around wells containing cells that produce immunoglobulin that is not bound by a cytokine receptor or receptor, and around wells containing cells producing immunoglobulin that is bound by a cytokine receptor or receptor, but binding between cytokine receptor or receptor and cytokine or ligand is not blocked, the immunoglobulin diffusing from the wells binds, but the binding of cytokine receptor or receptor to the cytokine or ligand is not blocked. Such wells can be distinguished from wells containing cells producing immunoglobulin. Target cells in the form of antigen-specific immunoglobulin-producing cells can thus be specified.

The above method will be described based on FIG. 3.

(A) A receptor is coated on the chip surface.

(B) Antibody-secreting cells are added to the microwells and cultured. The antibody that is secreted diffuses. The receptor-specific antibody binds to the receptor around the wells.

(C) When the antibody that has bound to the receptor binds to a ligand-binding site, fluorescence-labeled ligand cannot bind to the receptor.

(D) When the antibody that has bound to the receptor binds to something other than a ligand-binding site, fluorescence-labeled ligand is able to bind to the receptor.

[The Method for Producing Target Cells]

The present invention includes a method for producing target cells comprising recovering from the wells target cells that have been specified by the above-described screening method of the present invention. The target cells can be specific immunoglobulin-producing cells or specific cytokine-producing cells.

The present invention permits the preparation of an antigen-specific antibody protein by recovering an antigen-specific immunoglobulin gene from a recovered target cell, expressing antibody cDNA and preparing an antigen-specific antibody protein. Further, the mRNA of a T cell receptor gene expressed by a cell that has produced a cytokine can be recovered, and the T cell receptor cDNA can be recovered and introduced into another cell to express a T cell receptor protein.

EMBODIMENTS

The present invention is described in greater detail below based on embodiments.

An example of the preparation of a microwell array chip will be described.

Preparation Example 1

A preparation example employing a silicon base plate will be described. FIG. 4-1 is an example of a microwell array chip based on Preparation Example 1. Examples of the preparation steps are shown in FIG. 4-2.

(1) An oxide film 1-a is formed on a silicon base plate 1-b.
(2) A photoresist 1-c, such as OFPR-800 from Tokyo Ohka Kogyo Co., Ltd., is applied on the base plate and an exposure device is used to transfer a pattern.
(3) Oxide film 1-a that is exposed through photoresist 1-c is etched with buffered hydrofluoric acid.
(4) Microwells 1-d that are 10 to 20 microns in depth are formed by dry etching or wet etching. Photoresist 1-c is suitably removed based on the etching method.
(5) The surface is treated with primer so that antibodies will bind uniformly. For example, a silylation treatment is used to form silyl groups 1-e on the surface and inner walls of the wells. There are various materials and methods that can be employed in this treatment; they are not limited by the treatment employed in the present preparation example.
(6) The detection of antibody-secreting cells is conducted based on the present invention.

Preparation Example 2

To more clearly monitor the antibodies that are secreted by cells, it is possible to provide partitions around wells. FIG. 5-1 shows the external appearance of such a partition and FIG. 5-2 shows a preparation example.

(1) An oxide film 2-a is formed on a silicon base plate 2-b.
(2) A photoresist 2-c, such as OFPR-800 from Tokyo Ohka Kogyo Co., Ltd., is applied on the base plate and an exposure device is used to transfer a pattern.
(3) Oxide film 2-a that is exposed through photoresist 2-c is etched with buffered hydrofluoric acid.
(4) Photoresist 2-c is removed and indentations 2-d that are 1 to 5 microns in depth are fabricated by etching.
(5) A photoresist 2-e, such as OFPR-800 from Tokyo Ohka Kogyo Co., Ltd., is applied again on the base plate and an exposure device is used to transfer a pattern. When the indentations are deep, a negative resist such as OMR-85 from Tokyo Ohka Kogyo Co., Ltd. can be employed.
(6) Wells 2-f that are 10 to 20 microns in depth are formed with a dry etcher.
(7) The surface is treated with primer so that antibodies will bind uniformly. For example, a silylation treatment is used to form silyl groups 2-g on the surface and inner walls of the wells. There are various materials and methods that can be employed in this treatment; they are not limited by the treatment employed in the present preparation example.
(8) The detection of antibody-secreting cells is conducted based on the present invention. In the present example, since walls are formed around the wells to inhibit the diffusion of antibodies, muddling due to the diffusion of antibodies is inhibited, facilitating image identification.

FIG. 5-3 shows the result of a trial run of the present preparation example.

Preparation Example 3

By increasing the surface area around the wells, it is possible to more accurately observe antibodies that are secreted. The surface area can be increased by forming a porous silicon structure or an uneven structure, for example. Japanese Unexamined Patent Publication (KOKAI) Heisei No. 6-21509, for example, describes a method for preparing porous silicon. An uneven structure can be prepared by etching, vapor deposition, or the like. FIG. 6-1 shows the external appearance thereof, and FIG. 6-2 shows a preparation example thereof.

(1) An oxide film 3-a is formed on silicon base plate 3-b.
(2) A photoresist 3-c, such as OFPR-800 from Tokyo Ohka Kogyo Co., Ltd., is applied on the base plate and an exposure device is used to transfer a pattern.
(3) Oxide film 3-a that is exposed through photoresist 3-c is etched with buffered hydrofluoric acid.
(4) To increase the surface area of openings in exposed portions, a porous structure 3-d, for example, can be fabricated. The porous structure is formed by anode chemical conversion treatment or the like. A nanostructure can also be fabricated on the surface with a mixture of hydrofluoric acid and nitric acid.
(5) A photoresist 3-e, such as OFPR-800 from Tokyo Ohka Kogyo Co., Ltd., is applied again on the base plate and an exposure device is used to transfer a pattern. Dry etching is used to form wells 3-f that are 10 to 20 microns in depth.
(6) The surface is treated with primer so that antibodies will bind uniformly. For example, a silylation treatment is used to form silyl groups 3-g on the surface and inner walls of the wells. There are various materials and methods that can be employed in this treatment; they are not limited by the treatment employed in the present preparation example.
(7) The detection of antibody-secreting cells is conducted based on the present invention. In the present example, since the surface area is increased around the wells and since the density of fluorescence-labeled bonds is increased, fluorescence image identification is facilitated.

Preparation Example 4

By causing antibody to bind in localized fashion only around the wells, it is possible to observe antibody secretion more clearly. In the present method, a substance serving as a means of causing antibody to bind only around the wells can be achieved by termination using a pattern or the like. The external appearance thereof is shown in FIG. 7-1, and a preparation example is shown in FIG. 7-2. An oxide film 4-a is formed on a silicon substrate 4-b.

(1) A photoresist 4-c, such as OFPR-800 from Tokyo Ohka Kogyo Co., Ltd. is applied on the base plate and an exposure device is used to transfer a pattern.
(2) Oxide film 4-a that is exposed through photoresist 4-c is etched with buffered hydrofluoric acid.
(3) The surface is treated with primer so that antibodies will bind uniformly. For example, the surface is terminated with a silane coupling agent in the form of hexamethyldisilazane or the like. There are various materials and methods that can be employed in this treatment; they are not limited by the treatment employed in the present preparation example.
(4) A photoresist 4-e, such as OFPR-800 from Tokyo Ohka Kogyo Co., Ltd., is applied thereover.
(5) An antibody binding pattern is formed on photoresist 4-e with an exposure device. The dimension of the antibody binding pattern, which is greater than the wells, is from 1 micron to ½ the spacing of adjacent wells.
(6) Photoresist 4-e is processed into a well pattern with an exposure device.

(7) Dry etching is used to form wells 4-f that are 10 to 20 microns in depth in the well pattern. In the course of forming wells, substance 4-d that binds to antibody that is unprotected by photoresist 4-e is simultaneously removed. It can also be removed with oxygen plasma or the like.

(8) Photoresist 4-e is removed with an organic solvent such as acetone. Since the substance binding to antibodies is present only around the wells, the antibody binding range can be localized.

(9) The above steps can be simplified by employing a photosensitive silane coupling agent. Specifically, after conducting processing according to Preparation Example 1, the photosensitive silane coupling agent is applied and formed into a desired pattern by exposure to light to achieve the same results as in the present preparation example.

Fluorescence-labeled antibody was sown onto a microwell array chip produced according to the present preparation example. The binding state observed is shown in FIG. 7-3. Antibody binding was observed only in portions around the wells. Further, the present preparation example is characterized in that the antibody binding surface was formed only around the wells; there are various methods of achieving this. It is also possible to employ the dix series or the like made by Kishimoto Sangyo Co., Ltd. It forms amino groups on the surface of polyparaxylylene resin. The same binding surface can be realized as in the present preparation example. The same effect can also be achieved by forming a film having an effect that is the reverse of that of the primer for antibody binding on portions other than the antibody binding surface as needed. An example is Biosurfine, made by Toyo Gosei Co., Ltd.

The Surface Treatment Method (FIG. 8)

A surface treatment is conducted by the following method to cause anti-Ig antibody to bind uniformly.

1. Grime, such as oil, on the surface of base plate 5-a is removed. The grime is removed, for example, by cleaning with an organic solvent, acid, and alkali, or by dry cleaning with oxygen plasma or the like. The base plate material can be suitably selected based on the grime.

2. To increase the surface binding density of primer binding the base plate and an antibody, for example, it is also possible to form hydroxyl groups 5-b that substitute onto the primer on the surface of the base plate. To form hydroxyl groups on the surface of the base plate and remove microparticles from the surface, washing with about 1 percent ammonia water is conducted. Thorough rinsing with water is then conducted. In the case of silicon, it suffices to substitute this for SC-1 cleaning in RCA cleaning. However, 2. can be omitted if the formation of a surface suited to adequate primer binding can be achieved in 1.

3. Primer 5-c is bound to the surface. It is immersed in a silane coupling agent or the like, and adequately substituted with hydroxyl groups on the surface. The primer is, for example, hexamethyldisilazane, which renders the surface hydrophobic. There are various primer materials and methods that can be employed in this treatment; they are not limited to the surface treatment agent employed in the present preparation example.

The primer is chiefly characterized by being a silane coupling agent or a silylating agent, and by binding organic material to inorganic material. It is employed as a surface-modifying agent, and produces a hydrophobic surface. In semiconductors, materials typified by hexamethyldisilazane are primarily employed. The primer is needed to be suitably selected based on the base plate material. Examples are the silane coupling agents and silylating agents sold by Shin-Etsu Silicone.

The primer can be coated by a variety of methods. Dipping, spin coating, gas diffusion, $N_2$ bubbling, and the like are all possible. It is necessary to select the method best suited to the material. For example, in the case of gas diffusion, implementation is possible by exposure to an atmosphere of vaporized primer in a tightly sealed container for 5 to 10 minutes.

The microwell array chip of the present preparation example is not limited to silicon, and can be formed from resin, metal, glass, or the like. It need not be in the form of a single material, but can be in the form of a film formed on a base plate.

Examples of resins are acrylic, polypropylene, polyethylene, polyvinyl chloride, ABS, polyurethane, epoxy resin, thermosetting resins, photocuring resins, and photo-soluble resins. These resins can be molded by injection, compression, thermosetting, photocuring, dry etching, and the like. Molding can also be conducted by forming a resin film on a glass, silicon, or metal base plate. The surface of a resin that has been molded into the shape of microwells can be treated with primer in the same manner as silicon to bind antibody. For example, this can be realized by the surface treatment method described in the present invention. By using a photosensitive primer, it is possible to form an antibody binding pattern in the same manner as on silicon. Here, the primer employed is suitably selected while also considering its binding property to resin materials. If the resin itself functions to couple antibody to the surface thereof, and is capable of binding antibody, an even greater reduction in cost can be achieved.

Examples of metals are aluminum, aluminum alloys, copper alloys, gold, and stainless steel. These metals can be molded by molding in metal molds, etching, and the like. Molding can also be conducted by forming a metal film on a glass, silicon, or metal base plate. A surface of metal that has been molded into the shape of microwells can be treated with primer in the same manner as silicon to bind antibody. For example, this can be realized by the surface treatment method described in the present invention. Here, the primer employed is suitably selected while also considering its binding property to metal materials.

Microwells can be formed in glass by etching. Further, a film of resin, silicon, or metal can be formed on the surface to form microwells. The surface of a metal that has been molded into the shape of microwells can be treated with primer in the same manner as silicon to bind antibody. For example, this can be realized by the surface treatment method described in the present invention. Here, the primer employed is suitably selected while also considering its binding property to glass and surface-film forming materials.

In the embodiments below, silicon microwell array chips fabricated according to Preparation Example 1 were employed. However, the surface shape of the wells of the chips employed in the embodiments was hexagonal (round in Preparation Example 1).

Embodiment 1

Experimental Method

Protocol I

1. [Applying a coating on an anti-human IgG chip] An 80 μL quantity of anti-human IgG that had been diluted with PBS to 10 μg/mL was added to a silicon microwell array chip that had been treated with a silane coupling agent, the chip was placed in a moisture-conserving box (FIG. 9) to maintain the chip humidity so that the solution on the chip did not dry out, and the chip was left standing for one hour at room temperature (15 to 25° C.) to cause the anti-IgG antibody to bind to the surface of the silicon chip. In this case, in contrast to step 2 below, no degassing by pressure reduction was conducted. The antibody did not enter the wells, but was distributed around the wells. (Subsequently, while being incubated, the chip was constantly kept in the moisture-conserving box to prevent it from drying out.)

2. [Blocking] The antibody solution was removed from the chip, 100 μL of PBS was added to the chip and then removed in a cleaning operation that was repeated three times. Subsequently, 100 μL of PBS containing 0.2 percent (v/v) Lipidure (NOF Corporation, BL-B03 Lipidure (5 weight percent)) was added to the chip, and a vacuum pump was used to generate a vacuum to completely remove bubbles in the microwells, thereby covering the surface of the chip and filling the interior of the wells with Lipidure solution. The chip was left standing for 15 minutes at room temperature (15 to 25° C.) to conduct blocking.

3. [Adding cells] The chip was washed three times with 100 μL of RPMI 1640 medium containing 10 percent FCS. X63/116 cells (secreting human IgG in response to hepatitis B virus surface antigen (HBs antigen)) or HyHEL10 110TC cells (secreting mouse/human chimera antibody in response to chicken egg lysozyme (HEL)) that had been washed twice with RPMI 1640 medium containing 10 percent FCS were added to the chip and the chip was left standing at room temperature for about 10 minutes so that the cells entered the wells.

4. [Culturing the cells] Cells that had not entered the wells were removed by washing several times with RPMI 1640 medium containing 10 percent FCS (until all of the surplus cells had been removed). An 80 μL quantity of RPMI 1640 medium containing 10 percent FCS was added onto the chip, the chip was placed in a $CO_2$ incubator (37° C., 5 percent $CO_2$), and the cells were cultured on the chip for 2 to 3 hours.

5. [Binding biotin-labeled antigen] While taking care to prevent the cells from exiting the wells, the buffer was removed from the chip surface, about 100 μL of PBS was added to the surface of the chip and then removed, and this operation was repeated several times to clean the chip. Subsequently, an 80 mL quantity of 1 mg/mL biotin-labeled HEL or biotin-labeled HBs antigen was added to the chip and the chip was left standing for 30 minutes at room temperature.

6. After washing the chip with PBS in the same manner as in 5, 80 μL of Cy3-labeled streptavidin (Sigma, S-6402) comprised of a 1,000-fold dilution of the original solution was added to the chip, and the chip was similarly left standing for 30 minutes at room temperature.

7. After washing the chip with PBS in the same manner as in 5, PBS was added to the chip, the fluorescence of the Cy3 was observed by fluorescence microscopy, and the positions of wells containing cells secreting antigen-specific antibody were determined based on the spreading of Cy3 fluorescence in the form of donuts around the wells (FIG. 10).

8. An 80 μL quantity of 1 μg/mL Oregon green was added to the chip and the chip was left standing for 3 minutes at room temperature to label the cells with Oregon green. After washing the chip with PBS in the same manner as in 5, fresh PBS was added to the chip. While observing the cells using the fluorescence of the Oregon green as an indicator, target cells that were secreting antigen-specific antibody were recovered with a micromanipulator.

Identification of Antigen-Specific Antibody-Secreting Cells on a Microwell Array Chip by the Method of the Present Invention (FLISPOT Method)

HyHEL10 110TC cells, X63/116 cells, and 110TC cells (negative control, did not secrete antibody) were cultured on silicon microwell array chips coated with anti-IgG antibody. The secretion of antigen-specific antibody was detected with biotin-labeled HEL or biotin-labeled HBs antigen and Cy3-labeled streptavidin (FIG. 11A). As indicated in FIG. 11A, the antibody that had been secreted was detected in the form of donuts around the wells. On the chip to which 110TC that did not secrete antibody had been added, no signal was detected. Oregon green was then used to stain the cells and the cells were confirmed (FIG. 11B).

The staining was antigen-specific. On the chip to which HyHEL10 110TC cells had been added, a signal was detected with biotin-labeled HEL, but no signal was detected with biotin-labeled HBs antigen. Conversely, on the chip to which X63/116 cells had been added, no signal was detected with biotin-labeled HEL, but a signal was detected with biotin-labeled HBs antigen (the data are not given).

Identification of Antigen-Specific Antibody-Secreting Hybridomas by the FLISPOT Method (Applying Protocol I)

Spleen cells were prepared from BALB/c mice that had been immunized with HEL protein. These cells were fused by the usual method employing polyethylene glycol with X63.Ag8.653 myeloma cells to create hybridomas. The hybridomas were selected with HAT selection medium and then added to a microwell array chip that had been coated with anti-mouse IgG antibody. The cells that did not enter the wells were removed by washing, after which the cells were cultured on the chip for 1 hour 30 minutes. Hybridomas secreting antibody to HEL were detected using biotin-labeled HEL and PE-labeled streptavidin (FIG. 11A). Oregon green was then added to determine the position of the cells (FIG. 11B). (FIG. 11C) A combination of A and B.

Embodiment 2

Experimental Method

Protocol II

Preparation of Mouse CD138 Positive Cells (Antibody-Secreting Cells)

1. Mouse spleen cells were prepared.
2. Anti-mouse CD138 antibody was added to a 100 μL cell suspension in a quantity of <1 μg per $10^6$ cells and the cells were incubated for 15 minutes at 4° C.
3. The cells were washed twice with 10 mL of PBS and then suspended in 100 μL of PBS. To the cell suspension was then added anti-rat κ(kappa)-chain antibody-bound microbeads in a quantity of <1 μg per $10^6$ cells and the cells were incubated for 15 minutes at 4° C.
4. The cells were washed twice with 10 mL of PBS and then suspended in 1,000 μL of PBS. CD138 positive cells were recovered with an AutoMACS.

Preparation of Human CD138 Positive Cells

1. Lymphocytes were separated from human peripheral blood by an established method (the specific gravity centrifugation method employing Ficoll).
2. Fc receptor blocking reagent (Miltenyl Biotec Co., Ltd.) was added in a quantity of 20 μL per $10^7$ cells, followed by anti-CD138 antibody-bound microbeads in a quantity of <1 μg per $10^6$ cells and the cells were incubated for 15 minutes at 4° C.

3. The cells were washed twice with 10 mL of PBS and suspended in 1,000 μL of PBS. The CD138 positive cells were then recovered with an AutoMACS.

Experimental Method

Protocol II, Continued

1. In the tests below, the same measures were adopted to preventing drying out as in protocol I in the course of incubation.

2. To a silicon microwell array chip that had been treated with a silane coupling agent was added 80 μL of PBS-diluted 10 μg/mL donkey-derived anti-goat IgG antibody. The chip was placed in a moisture-conserving box (FIG. 1) so that the solution on the chip did not dry out, and left standing for 1 hour at room temperature (15 to 25° C.) to cause the donkey-derived anti-goat IgG antibody to bind to the surface of the silicon chip.

3. The antibody solution was removed from the chip, the chip was washed three times with 100 μL of PBS, 100 μL of PBS containing 0.2 percent (v/v) Lipidure (NOF Corporation, BL-B03 Lipidure (5 weight percent)) was added to the chip, and a vacuum was generated to remove bubbles in the microwells, thereby covering the surface of the chip and filling the interior of the wells with Lipidure solution. The chip was left standing for 15 minutes at room temperature to conduct blocking.

4. The chip was washed three times with 100 μL of RPMI 1640 medium containing 10 percent FCS. CD138 positive antibody-secreting cells (1 to $2\times10^6$ cells suspended in 30 μL of PBS) that had been washed once with 10 mL of PBS were added to the chip and the chip was left standing for about 10 minutes at room temperature to allow the cells to enter the wells.

5. Cells that had not entered the wells were removed by washing with RPMI 1640 medium containing 10 percent FCS. An 80 μL quantity of 10 μg/mL goat-derived anti-human (or mouse) IgG was then added to the chip and the chip was left standing for 30 minutes at room temperature to cause the antibody to bind to the donkey-derived goat IgG antibody on the chip surface.

6. The chip was washed with RPMI 1640 medium containing 10 percent FCS while taking care to prevent the cells from exiting the wells. An 80 μL quantity of RPMI 1640 medium containing 10 percent FCS was then added to the chip and the cells were cultured for 3 hours in a $CO_2$ incubator (37° C., 5 percent $CO_2$).

7. Subsequent steps in the form of step 5 and beyond in protocol I were then conducted.

Detection of HEL-Specific Antibody-Secreting Cells Among Mouse Spleen Cells Immunized with HEL by the Method of the Present Invention (FLISPOT Method)

CD138 positive cells were prepared from the spleen cells of BALB/c mice that had been immunized with chicken egg lysozyme (HEL). The cells were added to a silicon microwell array chip to which donkey-derived anti-goat IgG antibody had been bound according to protocol II. Subsequently, goat-derived anti-mouse IgG antibody was bound to the chip according to the protocol and the cells were cultured for about 3 hours. Subsequently, biotin-labeled HEL and Cy3-labeled streptavidin were added and the cells that were secreting HEL-specific IgG antibody were detected by fluorescence microscopy (FIG. 12). Subsequently, the cells were recovered with a micromanipulator and the antibody gene was amplified. Of the seven IgG's prepared, six bound to HEL (the data are not given).

Detection of HBs-Specific Antibody-Secreting Cells Among Human Peripheral Blood Lymphocytes by the Method of the Present Invention (FLISPOT Method)

CD138 positive cells were prepared by protocol II from healthy human peripheral blood that had been boosted with HBs antigen vaccine. The CD138 positive cells were added to a silicon microwell array chip to which donkey-derived anti-goat IgG antibody had been bound by protocol II. Subsequently, goat-derived anti-human IgG antibody was bound to the chip according to the protocol and the cells were cultured for about 3 hours. Biotin-labeled HBs antigen and Cy3-labeled streptavidin were then added and the cells that were secreting HBs antigen-specific IgG antibody were detected by fluorescence microscopy (FIG. 13).

Volunteers from whom informed consent had been obtained were inoculated with HBs vaccine, 100 mL of blood was drawn on day 7, CD138 positive cells were selected from peripheral blood lymphocytes obtained from this blood, and these cells were sown on a plate that had been coated with anti-human IgG. The cells were cultured, after which HBs-specific antibody-secreting cells were detected using biotin-labeled HBs antigen and Cy3-labeled streptavidin. Cells were recovered from a total of 24 wells. HBs-specific antibody-secreting cells were similarly detected from peripheral blood lymphocytes obtained by drawing 100 mL of blood on day 8 following HBs vaccination, and cells were recovered from 57 wells. From these cells, 53 pairs of antibody H chain and L chain cDNA were prepared. The cDNA was combined into an expression vector, the pairs of H chain and L chain were introduced into the genome of 293T cells (a cell strain derived from fetal human kidney), and the culture supernatant was recovered. Whether or not the antibody that had been secreted into the supernatant bound to HBs antigen was analyzed by ELISA. As a result, 41 antibody proteins were produced, of which 36 were HBs antigen-specific.

Embodiment 3

Experimental Method

Protocol III

1. An 80 μL quantity of antigen (HEL protein) that had been diluted with PBS to 10 μg/mL was added to a silicon microwell array chip that had been treated with a silane coupling agent. The chip was placed in a moisture-conserving box (FIG. 9) so that the solution on the chip would not dry out. The chip was left standing for 1 hour at room temperature (15 to 25° C.) to cause the HEL protein to bind to the surface of the silicon chip. (Each time the chip was subsequently incubated, it was placed in this box to prevent drying out.)

2. The antigen solution was removed from the chip and the chip was washed three times with 100 μL of PBS. A 100 μL quantity of PBS containing 0.2 percent (v/v) Lipidure (NOF Corporation, BL-B03 Lipidure (5 weight percent)) was added to the chip, and a vacuum was generated to remove bubbles in the microwells, thereby covering the surface of the chip and filling the interior of the wells with Lipidure solution. The chip was left standing for 15 minutes at room temperature to conduct blocking.

3. CD138 positive cells were prepared according to protocol II from mouse spleen cells inoculated with HEL.

4. The chip was washed with RPMI 1640 medium containing 10 percent FCS, after which CD138 positive cells (1 to $2\times10^6$ cells suspended in 30 μL of PBS) that had been washed once with 10 mL of PBS were added to the chip. The chip was then left standing for about 10 minutes to allow the cells to enter the wells.

5. Cells that had not entered wells were removed by washing with RPMI 1640 medium containing 10 percent FCS, after which 80 μL of RPMI 1640 medium containing 10 percent FCS was added to the chip. The chip was then placed in a $CO_2$ incubator (37° C., 5 percent $CO_2$) and the cells were cultured for 3 hours on the chip.

6. Taking care not to cause the cells to exit the wells, the buffer on the surface of the chip was removed, 100 μL of PBS was added to the surface of the chip, and this operation was repeated several times to clean the chip. Subsequently, 80 μL of 1 μg/mL Cy3-labeled anti-mouse IgG was added to the chip and the chip was left standing for 30 minutes at room temperature.

7. A chip identical to that in 6 was washed with PBS, PBS was added to the chip, and the fluorescence of the Cy3 was observed by fluorescence microscopy to determine the positions of wells containing cells that were secreting antigen-specific antibody using the spreading of Cy3 fluorescence in the shape of donuts around the wells as an indicator (FIG. 14).

8. An 80 μL quantity of Oregon green was added to the chip and the chip was left standing at room temperature for 3 minutes to label the cells with Oregon green. A chip identical to that in 6 above was washed with PBS, fresh PBS was added to the chip, and while observing the cells with the fluorescence of the Oregon green as indicator, the target cells that were secreting antigen-specific antibody were recovered with a micromanipulator.

Embodiment 4

Experimental Method

Application of Protocol IV

The Use of Antigen Labeled with Enzyme or Antibody Labeled with Enzyme Instead of Fluorescence-Labeled Antigen or Fluorescence-Labeled Antibody
Differences 1. After employing the action of an enzyme-labeled antigen or enzyme-labeled antibody, a buffer to which the substrate of the enzyme had been added was added to the chip and incubation was conducted at room temperature.

2. The product resulting from conversion of the substrate by the enzyme precipitated in ring form around the well. This was observed by optical microscopy, permitting the detection of antibody-secreting cells.
Enzyme: alkaline phosphatase; Substrate: BCIP/NBT Detection is also possible using an antigen or an antibody to which a quantum dot has been bound instead of a fluorescent pigment.
Detection of Cytokine-Producing Cells 1. Instead of causing anti-IgG antibody to bind to the chip, anti-cytokine antibody is caused to bind to the chip, T cells or the like that secrete cytokine are sown on the chip, and the production of cytokine is induced.

2. The cytokine that is secreted binds to the anti-cytokine antibody around the wells.

3. Next, when fluorescence or enzyme-labeled cytokine antibody is added, the rings of cytokine that binds around the wells can be detected and the cytokine-secreting T cells or the like can be detected.
Immuno Spot Assay Assay on Chip (ISAAC)
The Detection of Cytokine-Secreting Cells
Method 1. Lymphocytes were prepared from human peripheral blood and stimulated overnight in a $CO_2$ incubator (37° C., 5 percent $CO_2$) in the presence of 10 ng/mL phorbol myristate acetate (PMA) and 1 muM ionomycine.

2. The lymphocytes were recovered and washed, after which the cells were added to a microwell array chip that had been coated with anti-human IFN γ(gamma)-antibody. The chip was placed in a moisture-conserving box (FIG. 9) to prevent drying out, after which the cells were cultured for 5 hours in a $CO_2$ incubator (37° C., 5 percent $CO_2$).

3. The chip was washed with PBS-Tween20, biotin-labeled anti-human IFN γ (gamma)-antibody was added to the chip, and the chip was incubated for 30 minutes at room temperature in a moisture-maintaining box.

4. The chip was washed with PBS-Tween20, Cy3-labeled streptoavidin was added, and the chip was incubated for 30 minutes at room temperature in the moisture-maintaining box.

5. The chip was washed with PBS-Tween20 and the signal of the cytokine secreted was observed by fluorescence microscopy (2 second exposure).

The results are given in FIG. 15.

Embodiment 5

Obtaining Blocking Antibody

1. The same measures to prevent drying out were adopted as in protocol 1 in the course of incubating the chips in the following tests.

2. An 80 μL quantity of 10 μg/mL of TRAIL-R1/Fc diluted with PBS was added to a silicon microwell array chip that had been treated with a silane coupling agent, and the chip was placed in a moisture-conserving box (FIG. 9) so that the solution on the chip did not dry out. The chip was left standing for 1 hour at room temperature (15 to 25° C.) and the TRAIL-R1/Fc was bound to the surface of the silicon chip.

3. The antibody solution was removed from the chip and the chip was washed three times with 100 μL of PBS. A 100 μL quantity of PBS containing 0.2 percent (v/v) Lipidure (NOF Corporation, BL-B03 Lipidure (5 weight percent)) was added to the chip, and a vacuum was generated to remove bubbles in the microwells, thereby covering the surface of the chip and filling the interior of the wells with Lipidure solution. The chip was left standing for 15 minutes at room temperature to conduct blocking.

4. The chip was washed three times with 100 μL of RPMI 1640 medium containing 10 percent FCS. CD138 positive antibody-secreting cells that had been washed once with 10 mL and washed twice with 1,000 μL of RPMI 1640 medium containing 10 percent FCS (1 to $2\times10^6$ cells suspended in 30 μL of RPMI 1640 medium containing 10 percent FCS) were added to the chip, after which the chip was left standing for about 10 minutes at room temperature to allow the cells to enter the wells.

5. Taking care not to cause the cells to exit the wells, the chip was washed with RPMI 1640 medium containing 10 percent FCS, after which another 80 μL of RPMI 1640 medium containing 10 percent FCS was added to the chip.

The cells were then cultured for 3 hours in a $CO_2$ incubator (37° C., 5 percent $CO_2$).

6. Taking care not to cause the cells to exit the wells, the buffer was removed from the surface of the chip, the operation of adding about 100 µL of PBS to the chip surface and removing it was repeated several times to clean the chip, 80 µL of 1 µg/mL biotin-labeled TRAIL was added to the chip, and the chip was left standing for 30 minutes at room temperature.

7. After washing the chip with PBS in the same manner as in 6, 80 µL of Cy3-labeled streptavidin (Sigma, S-6402) comprising an original solution diluted 1,000-fold, was added to the chip, which was then similarly left standing for 30 minutes at room temperature.

8. After washing the chip with PBS in the same manner as in 6, PBS was added to the chip, and the fluorescence of the Cy3 was observed by fluorescence microscopy. The positions of wells containing cells that were secreting antibody that was being blocked between the TRAIL-R1/Fc and its ligand, TRAIL, were determined using an indicator in the form of black donut shapes where the fluorescence of Cy3 had not bound around wells on the surface of the chip that was bright red with Cy3 fluorescence.

9. An 80 µL quantity of 1 µg/mL Oregon green was added to the chip and the chip was left standing at room temperature for 3 minutes to label the cells with Oregon green. After washing the chip with PBS in the same manner as in 6, fresh PBS was added to the chip. While observing the cells with the fluorescence of Oregon green as an indicator, the target cells that were secreting antigen-specific antibody were recovered with a micromanipulator.

Embodiment 6

Application of Functional Antibody to Screening

Receptor protein was coated on the surface of a chip, and CD138 cells prepared from the spleen cells of mice that had been immunized with receptor protein were sown on the chip. The cells were cultured, after which biotin-labeled ligand and Cy3-labeled streptavidin were added. Biotin-labeled ligand and Cy3-labeled streptavidin was bound over nearly the entire surface of the chip. However, the binding of biotin-labeled ligand and Cy3-labeled streptavidin was blocked around the wells of cells producing a functional antibody that blocked the binding of receptor ligand, so these areas were dark. The results are shown in FIG. 16. Left: Detection results for biotin-labeled ligand/Cy3-labeled streptavidin. Middle: The cells were labeled with Oregon green and observed. Left: The left and middle figures superposed.

INDUSTRIAL APPLICABILITY

The present invention is useful in technical fields relating to methods of screening immune cells, such as specific immunoglobulin-producing cells and specific cytokine-producing cells. Examples are the fields of diagnosis and immunology-related pharmaceuticals, including antibody pharmaceuticals.

BRIEF DESCRIPTION OF THE DRAWINGS

FIG. 4-1 is a descriptive drawing of Preparation Example 1.

FIG. 4-2 is a descriptive drawing of Preparation Example 1.

FIG. 5-1 is a descriptive drawing of Preparation Example 2.

FIG. 5-2 is a descriptive drawing of Preparation Example 2.

FIG. 5-3 is a descriptive drawing of Preparation Example 2.

FIG. 6-1 is a descriptive drawing of Preparation Example 3.

FIG. 6-2 is a descriptive drawing of Preparation Example 3.

FIG. 7-1 is a descriptive drawing of Preparation Example 4.

FIG. 7-2 is a descriptive drawing of Preparation Example 4.

FIG. 7-3 is a descriptive drawing of Preparation Example 4.

Figure 1:
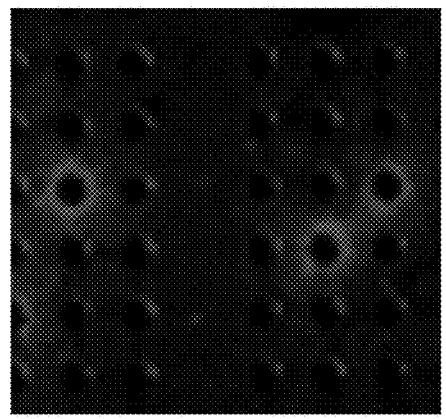
FIG. 1 is a drawing showing the relation between the form of the signal from a label substance and the shape of the well.
Figure 1:
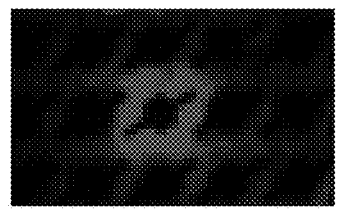
Figure 1:
Figure 1:
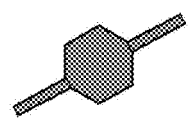
Figure 2:
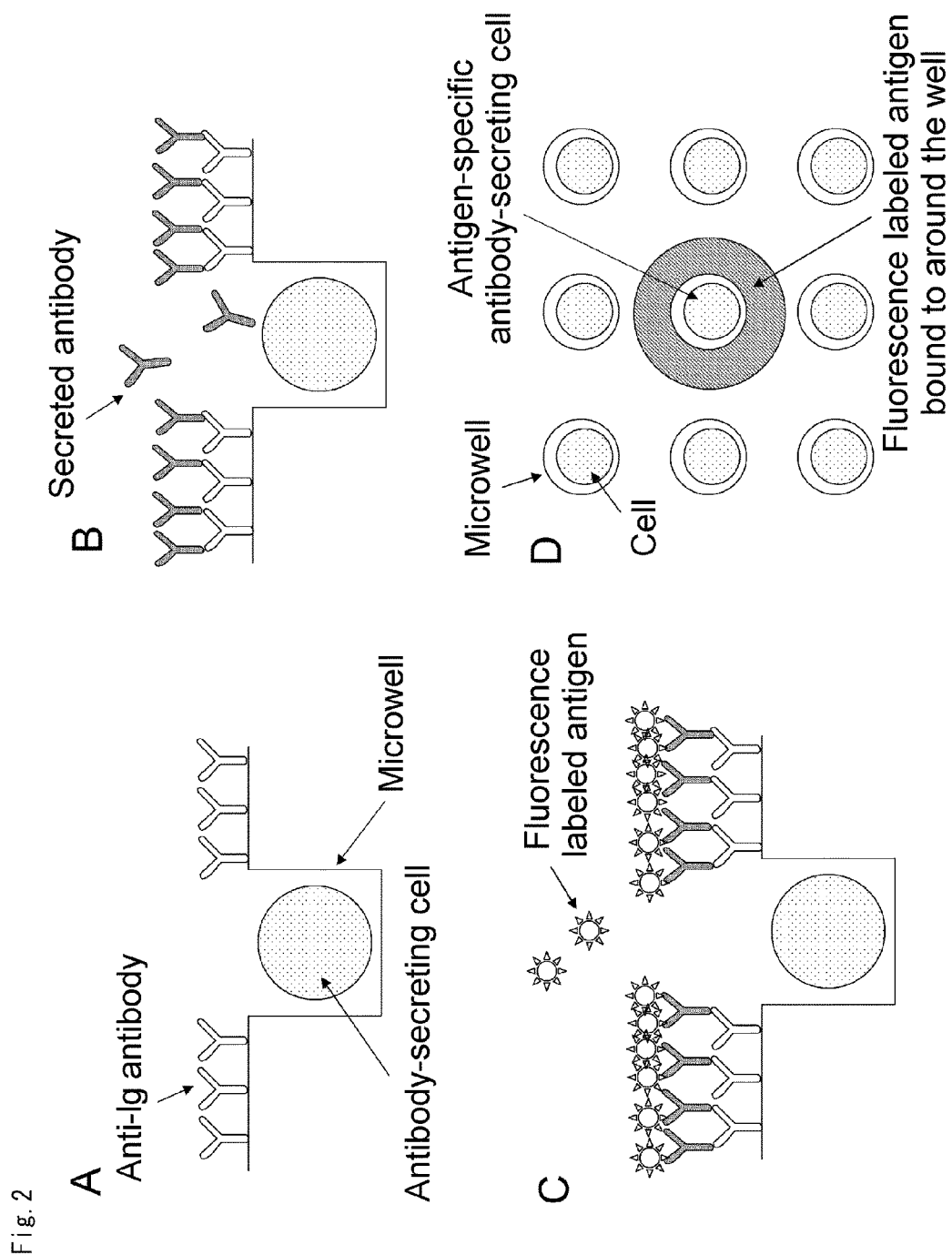
FIG. 2 is a descriptive drawing of the method of the present invention in an example employing antibody-secreting cells.
Figure 3:
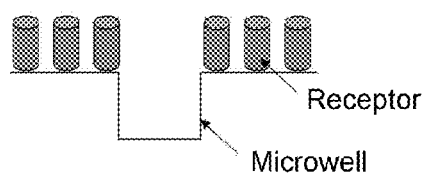
FIG. 3 is a descriptive drawing of the method of the present invention in case (1), in which the label substance binds specifically to a produced substance.
Figure 3:
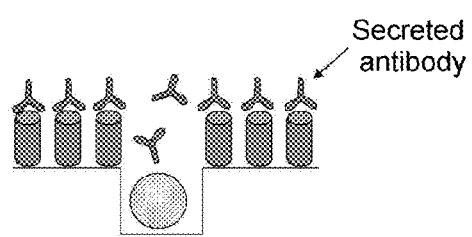
Figure 3:
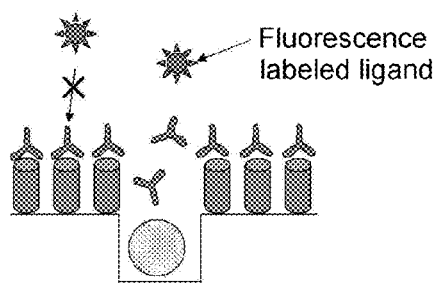
Figure 3:
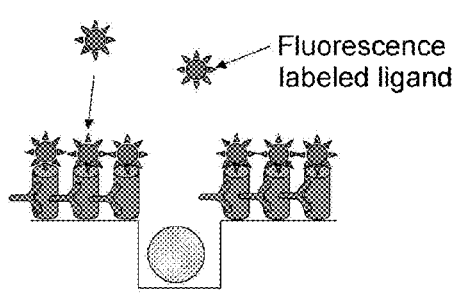
Figure 4:
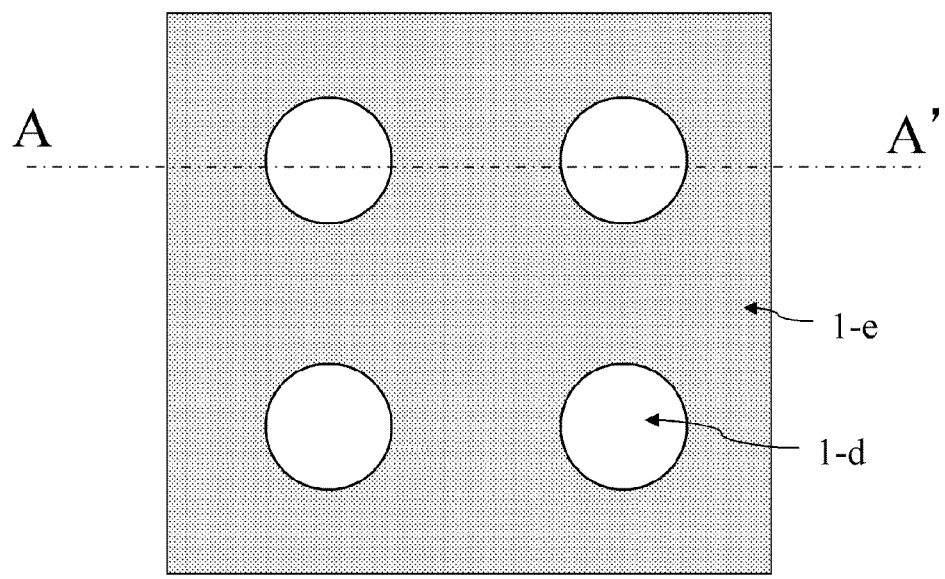
Figure 1:
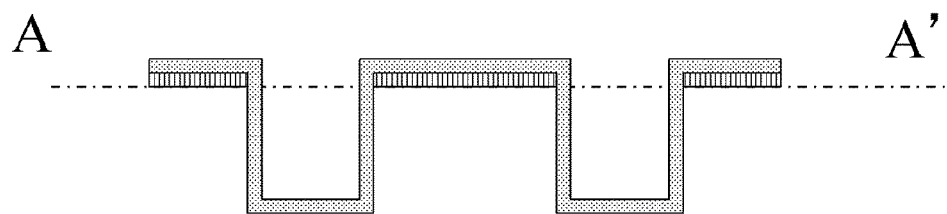
Figures 2, 5:
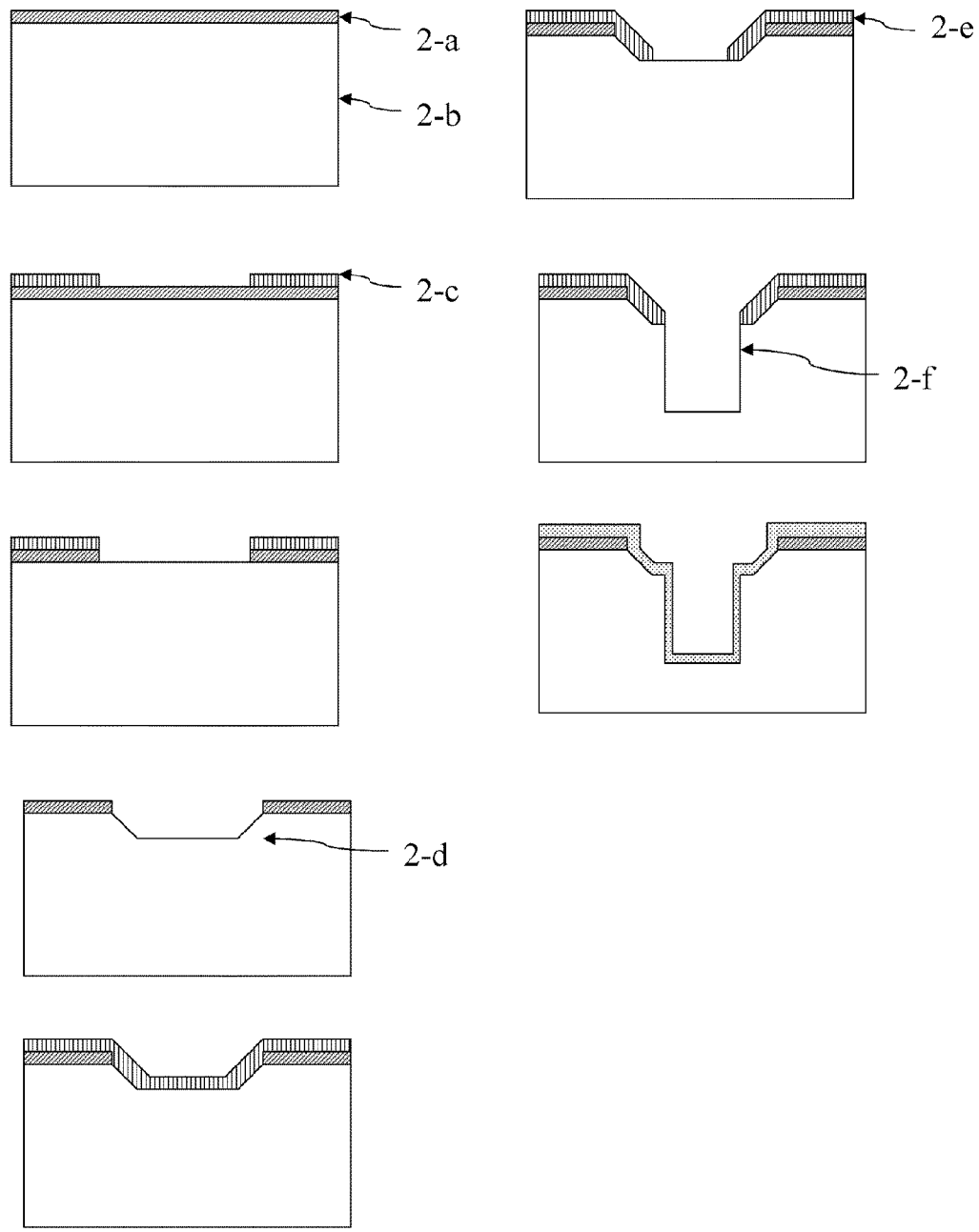
Figures 3, 5:
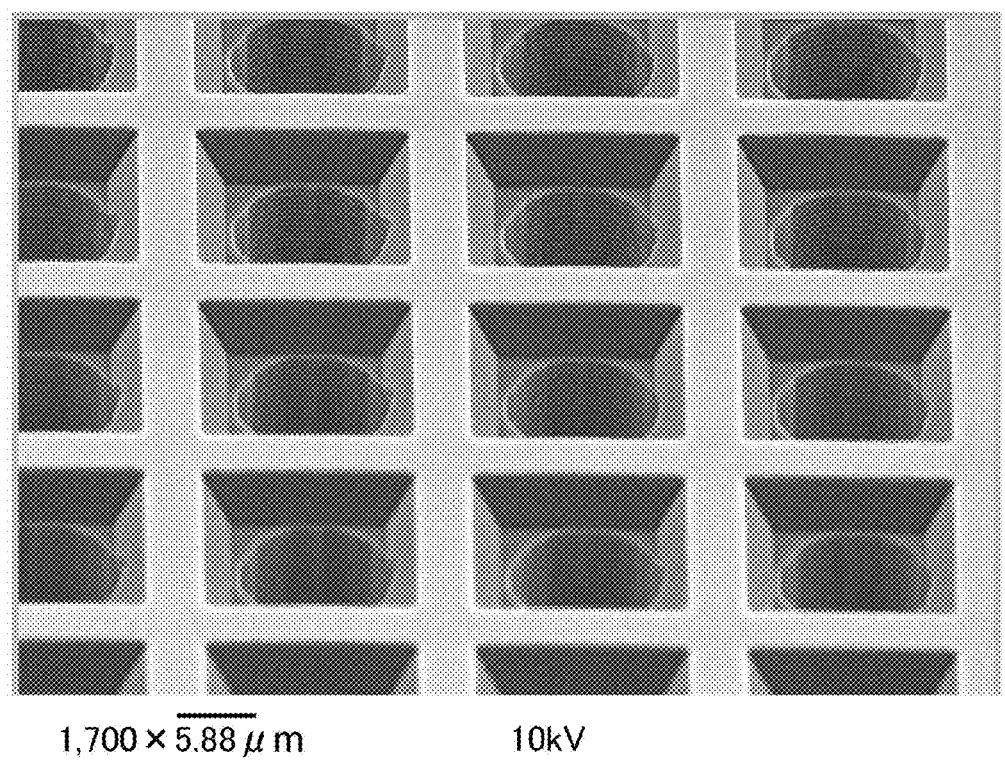
Figures 1, 6:
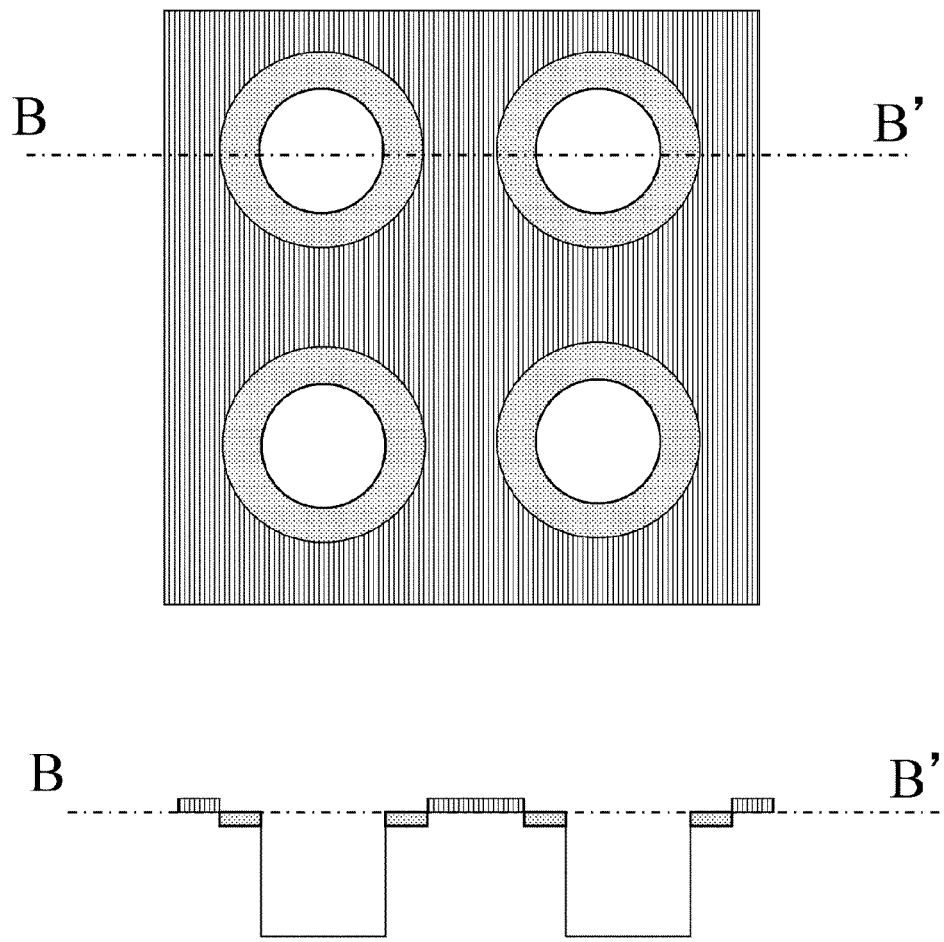
Figure 7:
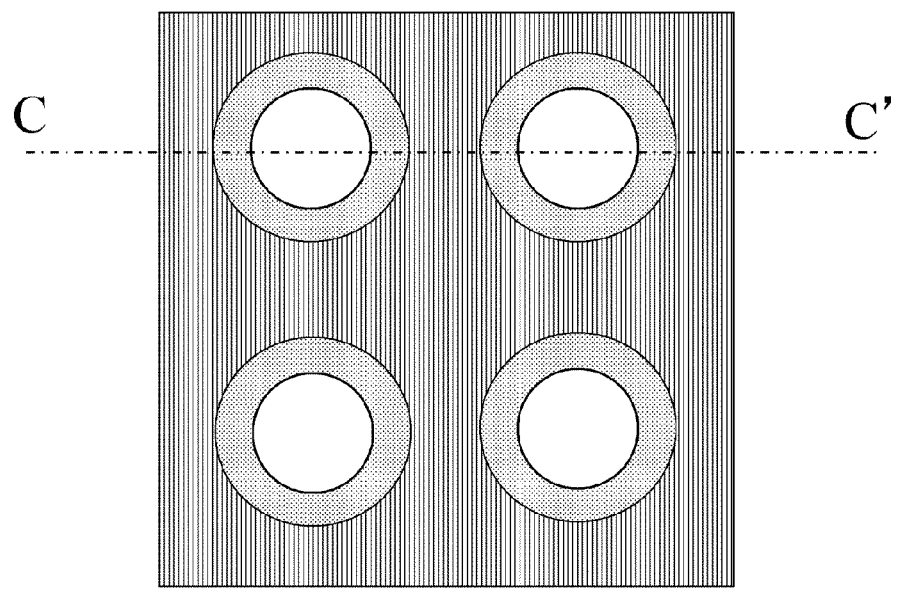
Figure 1:
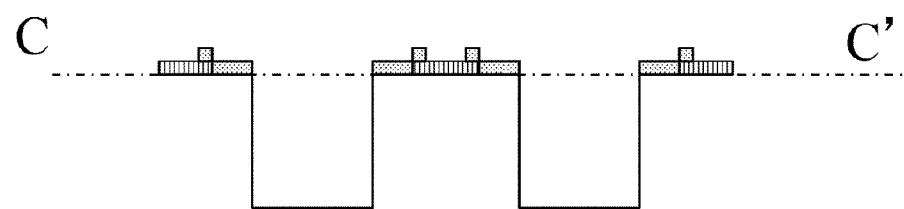
Figures 2, 7:
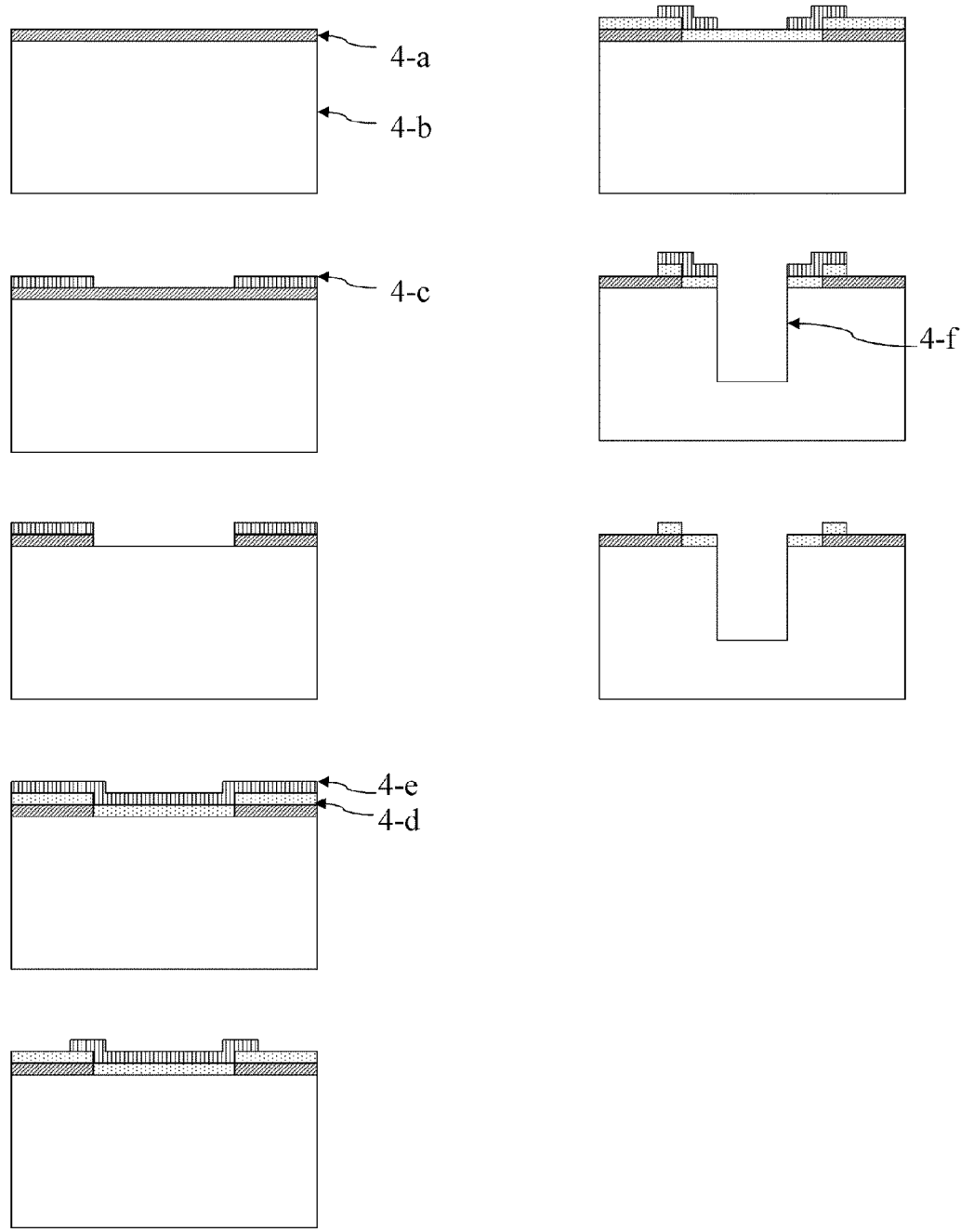
Figures 3, 7:
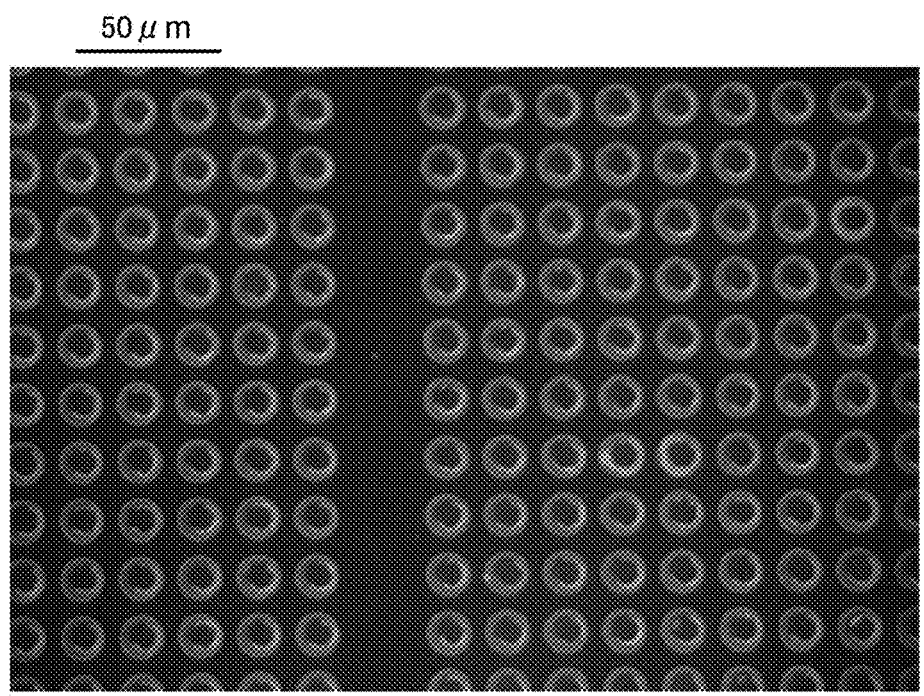
Figure 8:
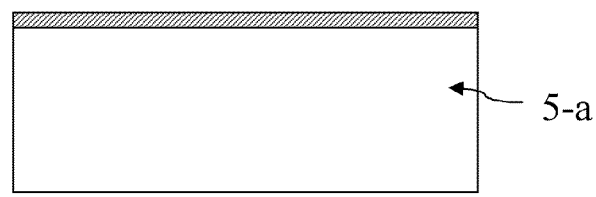
FIG. 8 is a descriptive drawing of a surface treatment method.
Figure 8:
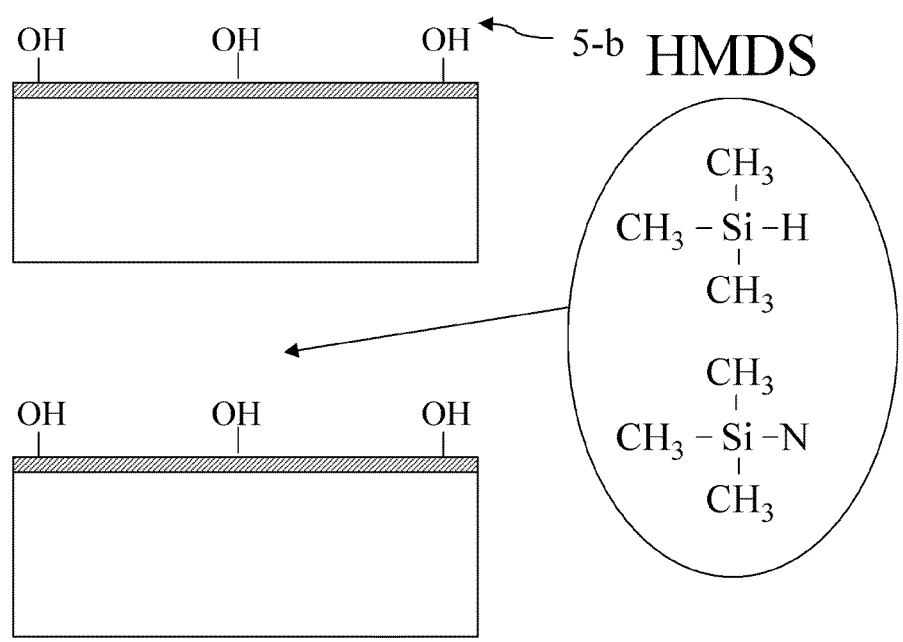
Figure 8:
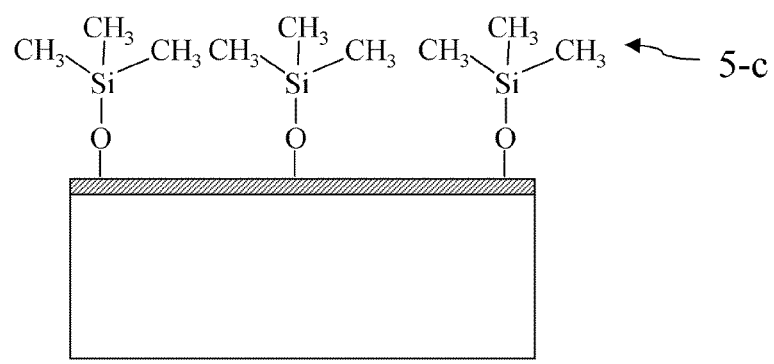
Figure 9:
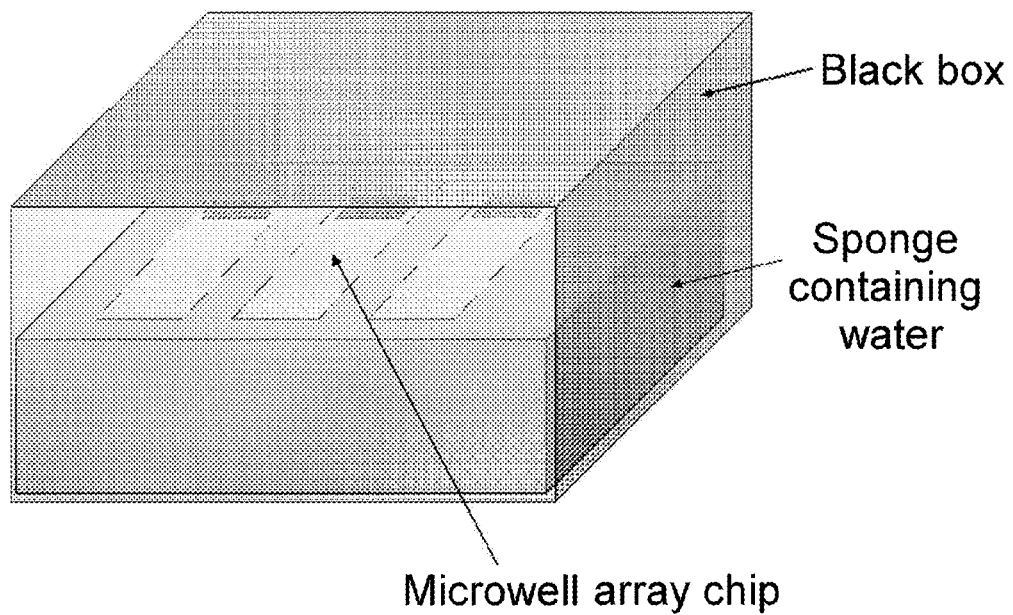
FIG. 9 is a descriptive drawing of a moisture-conserving box that maintains the humidity of the chip.
Figure 10:
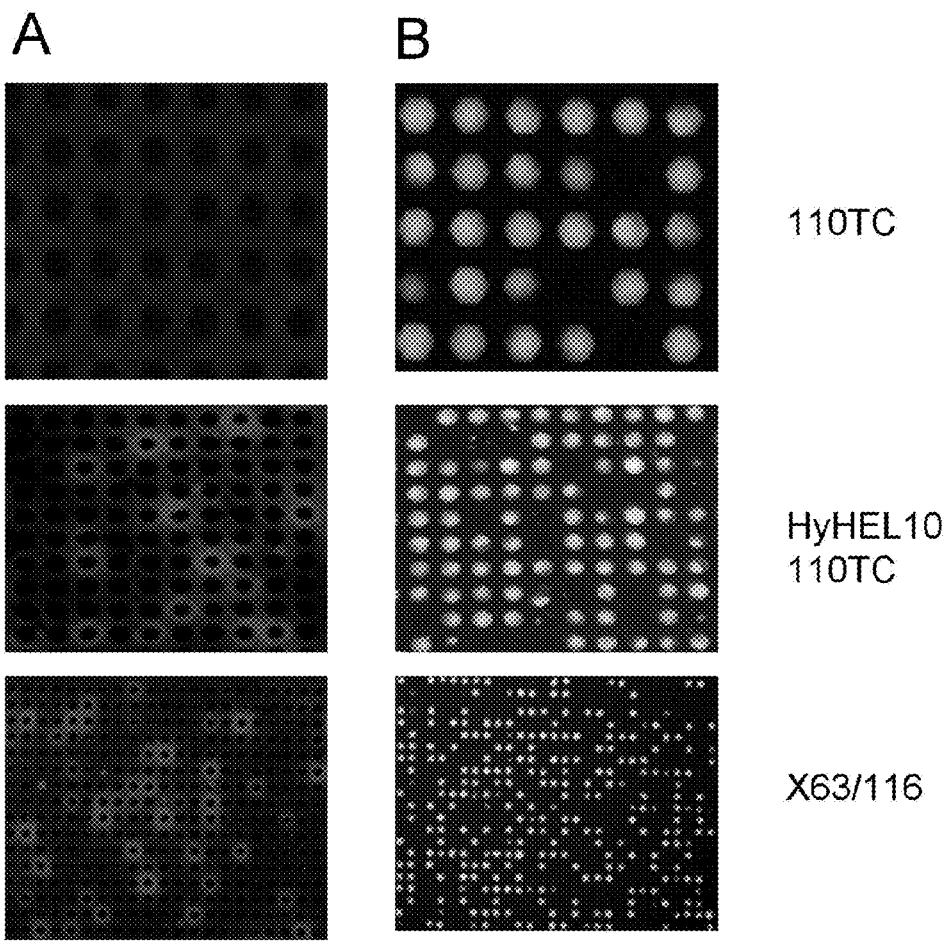
FIG. 10 shows the results of the determination of the positions of wells containing cells secreting antigen-specific antibodies in Embodiment 1.
Figure 11:
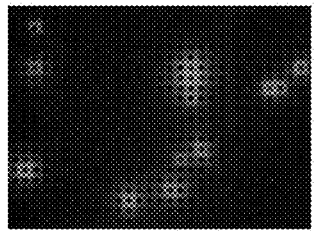
FIG. 11 shows the results of identification on a microwell array chip of antigen-specific antibody-secreting cells employed in the method (FLISPOT) of the present invention in Embodiment 1.
Figure 11:
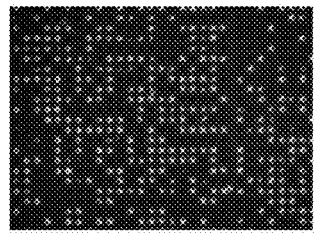
Figure 11:
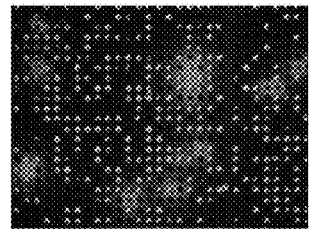
Figure 12:
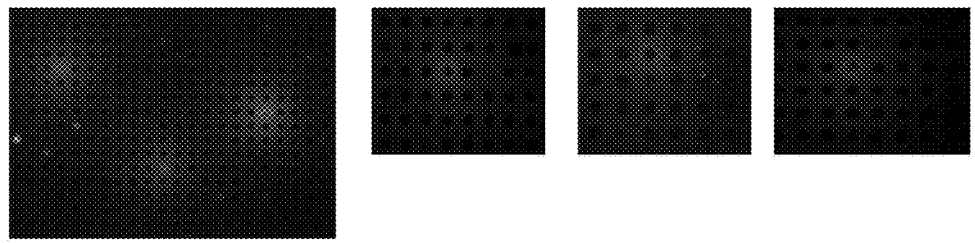
FIG. 12 shows the results of detection of HEL-specific antibody-secreting cells among mouse spleen cells immunized with HEL by the method (FLISPOT) of the present invention in Embodiment 2.
Figure 13:
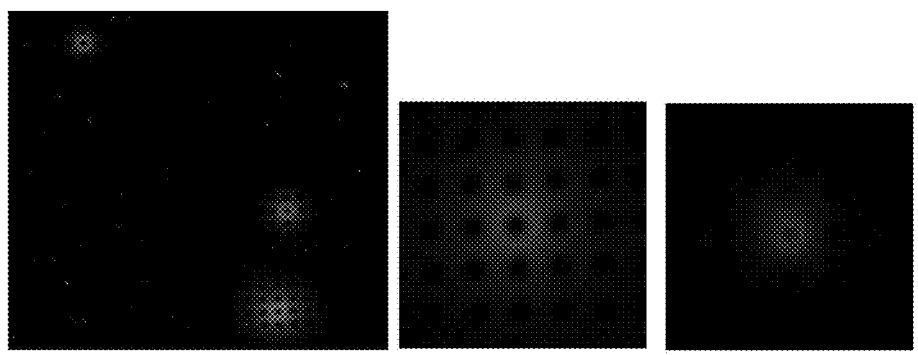
FIG. 13 shows the results of detection of HBs antigen-specific antibody-secreting cells among human peripheral blood lymphocytes by the method (FLISPOT) of the present invention in Embodiment 2.
Figure 14:
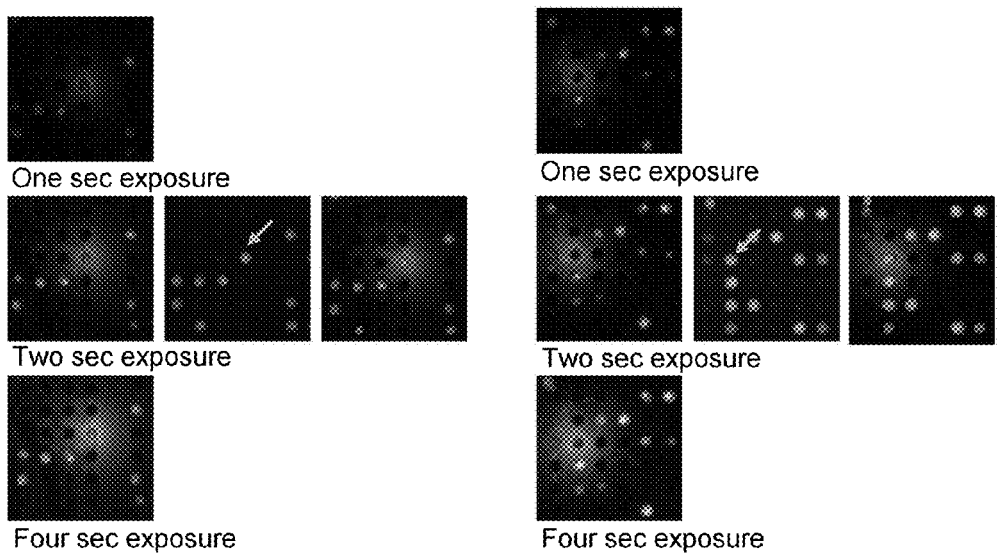
FIG. 14 shows the results of Embodiment 3.
Figure 15:
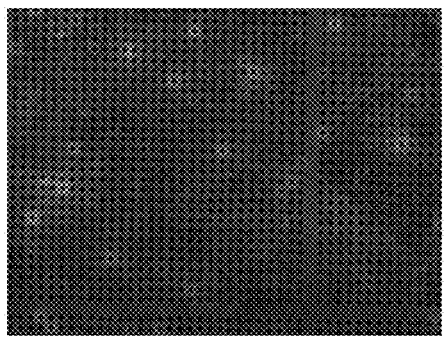
FIG. 15 shows the results of Embodiment 4 (the detection of cytokine-producing cells).
Figure 15:
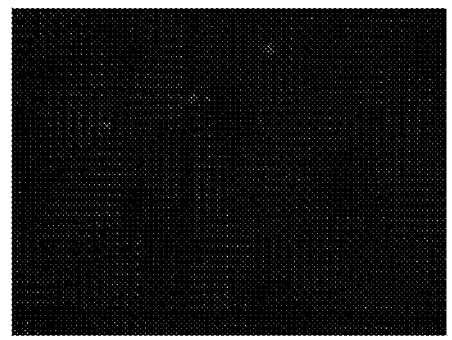
Figure 15:
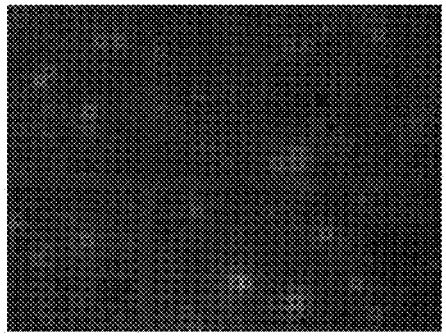
Figure 15:
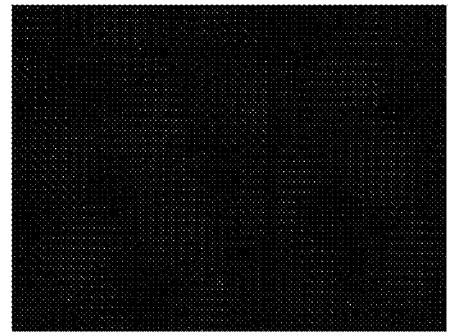
Figure 16:
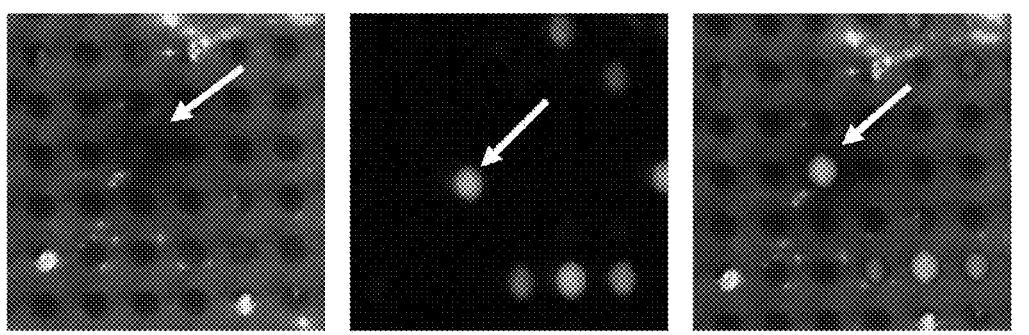
FIG. 16 shows the results of Embodiment 6 (the application of functional antibody to screening).
Figure 16:
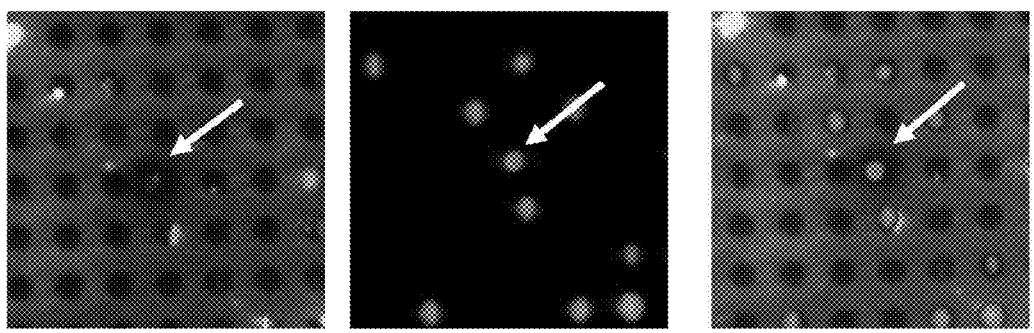

The invention claimed is:
1. A method of screening for a target cell, comprising:
causing specimen cells and a cell culture broth to be contained in at least a portion of the wells of a microwell array comprising multiple wells, each well being of a size permitting the entry of only a single cell therein, on one of the principal surfaces of a base member, wherein a coating layer of a binding substance having the ability to bind to at least a portion of a substance produced by a target cell is present only around the wells of said principal surface;
immersing the coating layer and the wells in the culture broth and culturing the cells in a state permitting the diffusion of said substance produced by said target cell in the culture broth from the wells into the coating layer;

after optionally removing the culture broth, feeding a label substance binding specifically to said substance produced by said target cell present among the specimen cells onto the coating layer; and detecting the binding of said substance produced by said target cell to said binding substance by means of said label substance in order to specify the well containing said target cell.

2. The screening method according to claim 1, wherein the cells present among the specimen cells include cells that have been stimulated with a desired antigen in advance and are in a state capable of producing a substance.

3. The screening method according to claim 1, wherein the specimen cells include immunoglobulin-producing cells or cytokine-producing cells.

4. The screening method according to claim 1, wherein the specimen cells include immunoglobulin-producing cells, said binding substance is an anti-immunoglobulin antibody or antigen, and the target cell is an antigen-specific immunoglobulin-producing cell.

5. The screening method according to claim 4, wherein the detection of the presence or absence of the binding is conducted using antigen or an antibody to the immunoglobulin that is produced.

6. The screening method according to claim 1, wherein the specimen cells include cytokine-producing cells, said binding substance is an anti-cytokine antibody or a cytokine receptor, and the target cell is an antigen-specific cytokine-producing cell.

7. The screening method according to claim 6, wherein the detection of the presence or absence of the binding is conducted using an antibody to the cytokine produced or a cytokine receptor.

8. The screening method according to claim 4 or 6, wherein the immunoglobulin-producing cells and cytokine-producing cells are natural cells, hybridomas, or cell strains.

9. A method for obtaining a target cell producing a given substance, wherein said target cell is from a group of cells containing specimen cells, comprising the steps of:

causing said specimen cells and a cell culture broth to be contained in at least a portion of wells of a microwell array,
wherein said microwell array comprises multiple wells on a principal surface of a base member, each well being of a size permitting the entry of only a single cell therein,
wherein a coating layer of a binding substance having the ability to bind to at least a portion of said substance produced by said target cell is bound on said principal surface, and
wherein said binding substance is present only around the wells on said principal surface;

immersing the coating layer and the wells in the culture broth and culturing the cells in a state permitting the diffusion of said substance produced by said target cell in the culture broth from the wells into the coating layer;

after optionally removing the culture broth, feeding a label substance binding specifically to said substance produced by said target cell present among the specimen cells onto the coating layer;

detecting the binding of said substance produced by said target cell to said binding substance by means of said label substance in order to specify the well containing said target cell; and recovering said target cell from a well thus specified.

10. The method according to claim 9, wherein said target cell is a specific immunoglobulin-producing cell or specific cytokine-producing cell.

11. The method according to claim 9, wherein the cells present among the specimen cells include cells that have been stimulated with a desired antigen prior to introduction into the wells of said microarray and are in a state capable of producing a substance.

12. The method according to claim 9, wherein said target cell is an antigen-specific immunoglobulin-producing cell and said binding substance is an antigen or an anti-immunoglobulin antibody.

13. The method according to claim 12, wherein said label substance is said specific antigen or an anti-immunoglobulin antibody.

14. The method according to claim 9, wherein said target cell is an antigen-specific cytokine-producing cell and said binding substance is an antibody to said cytokine, or a cytokine receptor.

15. The method according to claim 14, wherein said label substance is an antibody to said cytokine, or a cytokine receptor.

16. The method according to claim 10, wherein said immunoglobulin-producing cells or cytokine-producing cells are selected from the group consisting of primary cells, hybridomas, and cell lines.

17. The method according to claim 9, wherein the multiple wells are recesses formed within the principal surface of the base member.

18. The method according to claim 9, wherein said target cell is a mammalian cell.

19. The method according to claim 9, wherein the wells have a diameter of 4 micrometers to 15 micrometers.

20. The method according to claim 9, wherein the wells have a diameter in a range of 0.5 to 2 times a diameter of the cell.

21. A method for obtaining a target cell producing a given substance, wherein said target cell is from a group of cells containing specimen cells, comprising the steps of:

providing a microwell array wherein said microwell array comprises multiple wells and is formed on a principal surface of a base member, each well being of a size permitting the entry of only a single cell therein, said microwell array comprising a coating layer of a binding substance having the ability to bind to at least a portion of said substance produced by said target cell on said principal surface around the wells;

causing said specimen cells and a cell culture broth to be contained in at least a portion of the wells with the coating layer around the wells;

immersing the coating layer and the wells in the culture broth and culturing the cells in a state permitting the diffusion of said substance produced by said target cell in the culture broth from the wells into the coating layer;

after optionally removing the culture broth, feeding a label substance binding specifically to said substance produced by said target cell present among the specimen cells onto the coating layer;

detecting the binding of said substance produced by said target cell to said binding substance by means of said label substance in order to specify the well containing said target cell; and recovering said target cell from a well thus specified.

* * * * *